US010920212B2

(12) United States Patent
Chenal et al.

(10) Patent No.: US 10,920,212 B2
(45) Date of Patent: Feb. 16, 2021

(54) MONOMERIC AND FUNCTIONAL ADENYLATE CYCLASE CYAA TOXIN

(71) Applicant: INSTITUT PASTEUR, Paris (FR)

(72) Inventors: Alexandre Chenal, Ivry-sur-Seine (FR); Véronique Ntsogo Enguene, Paris (FR); Audrey Hessel, Grenoble (FR); Johanna Karst-Spiaczka, Roissard (FR); Daniel Ladant, Cachan (FR)

(73) Assignee: INSTITUT PASTEUR, Paris (FR)

( * ) Notice: Subject to any disclaimer, the term of this patent is extended or adjusted under 35 U.S.C. 154(b) by 0 days.

(21) Appl. No.: 15/326,633

(22) PCT Filed: Jul. 17, 2015

(86) PCT No.: PCT/EP2015/066494
§ 371 (c)(1),
(2) Date: Jan. 16, 2017

(87) PCT Pub. No.: WO2016/009080
PCT Pub. Date: Jan. 21, 2016

(65) Prior Publication Data
US 2018/0208919 A1 Jul. 26, 2018

(30) Foreign Application Priority Data
Jul. 17, 2014 (EP) .................................. 14306162

(51) Int. Cl.
C12N 9/88 (2006.01)
C07K 14/235 (2006.01)
A61P 11/14 (2006.01)

(52) U.S. Cl.
CPC ................ *C12N 9/88* (2013.01); *A61P 11/14* (2018.01); *C07K 14/235* (2013.01); *C12Y 406/01001* (2013.01)

(58) Field of Classification Search
None
See application file for complete search history.

(56) References Cited

FOREIGN PATENT DOCUMENTS

| EP | 2233569 A1 | 9/2010 | |
|---|---|---|---|
| WO | 99/26975 A2 | 6/1999 | |
| WO | 99/26975 A3 | 6/1999 | |
| WO | 02/22169 A2 | 3/2002 | |
| WO | 02/22169 A3 | 3/2002 | |
| WO | 02/062827 A2 | 8/2002 | |
| WO | 02/062827 A3 | 8/2002 | |
| WO | WO-2005089792 A1 * | 9/2005 | ........... C07K 14/005 |
| WO | 2005/033555 A2 | 3/2008 | |
| WO | 2008/033555 A3 | 3/2008 | |

OTHER PUBLICATIONS

Rogel et al. The Journal of Biological Chemistry. vol. 263, No. 26, Issue of Sep. 15, pp. 13310-13316, 1988.*
Lee, Sang-Jin ( Oligomerization of adenylate cyclase toxin from Bordetella pertussis. Dissertation. University of Virginia May 2001.*
Cheung et al. Infection and Immunity, Dec. 2006, vol. 74, No. 12, pp. 6797-6805.*
Ladant, D., Brezin, C., Alonso, J.M., Crenon, I., and Guiso, N. (1986) Bordetella pertussis adenylate cyclase. Purification, characterization, and radioimmunoassay. J Biol Chem 261, 16264-16269.
Karimova, G., Fayolle, C., Gmira, S., Ullmann, A., Leclerc, C., and Ladant, D. (1998) Charge-dependent translocation of Bordetella pertussis adenylate cyclase toxin into eukaryotic cells: implication for the in vivo delivery of CD8(+) T cell epitopes into antigen-presenting cells. Proc Natl Acad Sci USA 95, 12532-12537.
Chenal, A., Karst, J. C., Sotomayor Perez, A. C., Wozniak, A. K., Baron, B., England, P., and Ladant, D. (2010) Calcium-induced folding and stabilization of the intrinsically disordered RTX domain of the CyaA toxin. Biophys J 99, 3744-3753.
Sotomayor Perez, A. C., Karst, J. C., Davi, M., Guijarro, J. I., Ladant, D., and Chenal, A. (2010) Characterization of the regions involved in the calcium-induced folding of the intrinsically disordered RTX motifs from the bordetella pertussis adenylate cyclase toxin. Journal of molecular biology 397, 534-549.
Karst, J. C., Sotomayor Perez, A. C., Guijarro, J. I., Raynal, B., Chenal, A., and Ladant, D. (2010) Calmodulin-induced conformational and hydrodynamic changes in the catalytic domain of Bordetella pertussis adenylate cyclase toxin. Biochemistry 49, 318-328.
Chenal, A., Guijarro, J. I., Raynal, B., Delepierre, M., and Ladant, D. (2009) RTX calcium binding motifs are intrinsically disordered in the absence of calcium: implication for protein secretion. J Biol Chem 284, 1781-1789.
Sotomayor-Perez, A. C., Ladant, D., and Chenal, A. (2011) Calcium-induced folding of intrinsically disordered repeat-in-toxin (RTX) motifs via changes of protein charges and oligomerization states. J Biol Chem 286, 16997-17004.
Karst, J. C., Sotomayor-Perez, A. C., Ladant, D., and Chenal, A. (2012) Estimation of intrinsically disordered protein shape and time-averaged apparent hydration in native conditions by a combination of hydrodynamic methods. Methods in molecular biology 896, 163-177.
Sotomayor-Perez, A. C., Karst, J. C., Ladant, D. , and Chenal, A. (2012) Mean net charge of intrinsically disordered proteins: experimental determination of protein valence by electrophoretic mobility measurements. Methods in molecular biology 896, 331-349.
Karst, J. C., Barker, R., Devi, U., Swann, M. J., Davi, M., Roser, S. J. , Ladant, D., and Chenal, A. (2012) Identification of a region that assists membrane insertion and translocation of the catalytic domain of Bordetella pertussis CyaA toxin. J Biol Chem 287, 9200-9212.
Ladant, D., and Ullmann, A. (1999) Bordatella pertussis adenylate cyclase: a toxin with multiple talents. Trends in microbiology 7, 172-176.

(Continued)

*Primary Examiner* — Oluwatosin A Ogunbiyi
(74) *Attorney, Agent, or Firm* — Arrigo, Lee, Guttman & Mouta-Bellum LLP

(57) ABSTRACT

The present invention discloses a procedure to produce a monomeric and functional form of *Bordetella* sp, especially *B. pertussis*, CyaA toxin that can be stably maintained in this functional monodisperse state, even in the absence of any chaotropic agent.

Figure 1:
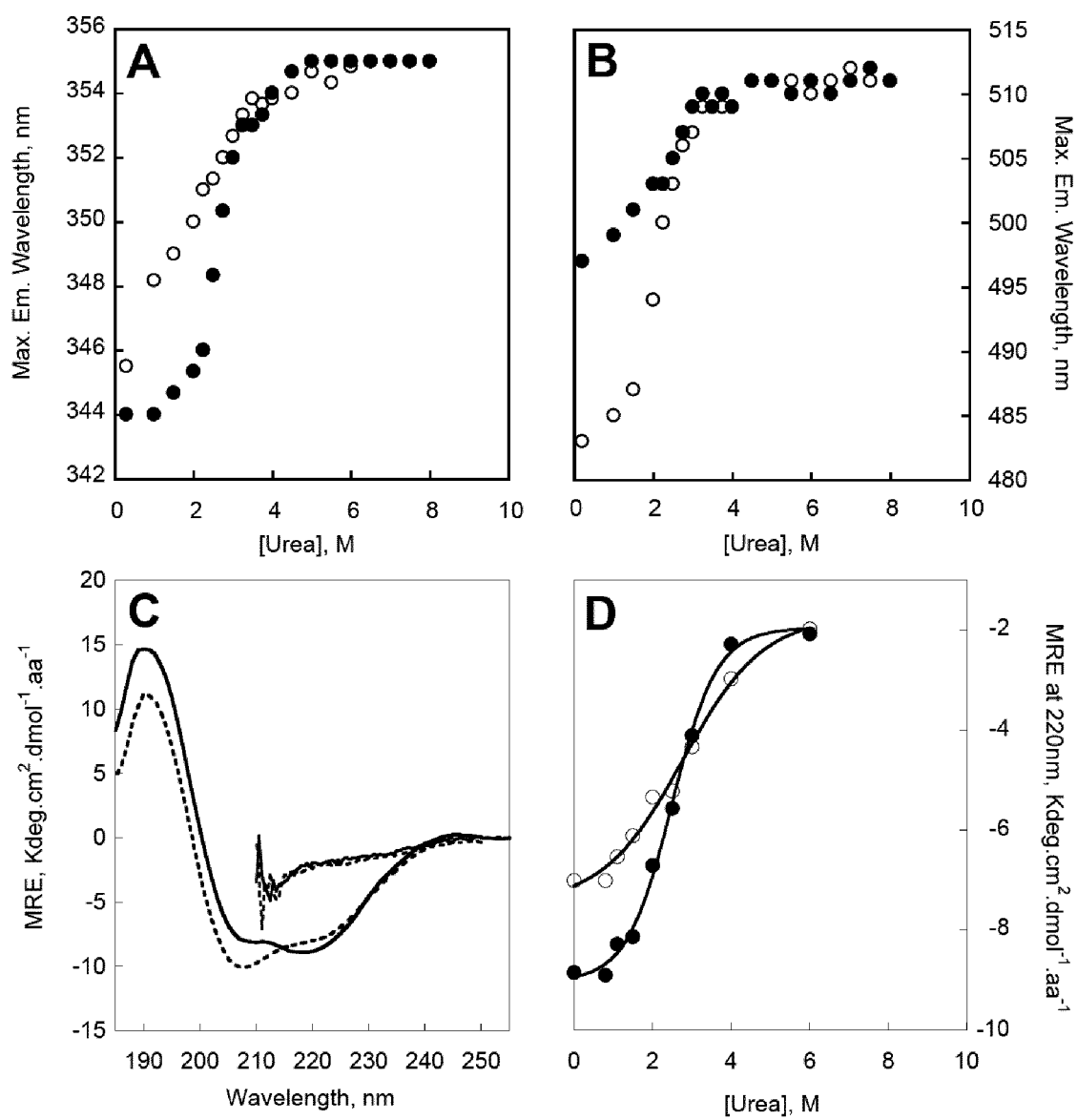

16 Claims, 19 Drawing Sheets
Specification includes a Sequence Listing.

(56) References Cited

OTHER PUBLICATIONS

Vojtova, J., Kamanova, J., and Sebo, P. (2006) Bordetella adenylate cyclase toxin: a swift saboteur of host defense. Curr Opin Microbial 9, 69-75.
Sakamoto, H., Bellalou, J., Sebo, P., and Ladant, D. (1992) Bordetella pertussis adenylate cyclase toxin. Structural and functional independence of the catalytic and hemolytic activities. J Biol Chem 267, 13598-13602.
Subrini, 0., Sotomayor-Perez, A. C., Hessel, A. , Spiaczka-Karst, J., Selwa, E, Sapay, N., Veneziano, R., Pansieri, J., Chopineau, J., Ladant, D., and Chenal, A. (2013) Characterization of a membrane-active peptide from the Bordetella pertussis CyaA.
Barry, E. M., Weiss, A. A., Ehrmann, I. E., Gray, M. C., Hewlett, E. L., and Goodwin, M. S. (1991) Bordetella pertussis adenylate cyclase toxin and hemolytic activities require a second gene, cyaC, for activation. J Bacterial 173, 720-726.
Welch, R. A. (2001) RTX toxin structure and function: a story of numerous anomalies and few analogies in toxin biology. Current topics in microbiology and immunology 257, 85-111.
Linhartova, I., Bumba, L., Masin, J., Basler, M., Osicka, R., Kamanova, J., Prochazkova, K., Adkins, I., Hejnova-Holubova, J., Sadilkova, L., Morova, J., and Sebo, P. (2010) RTX proteins: a highly diverse family secreted by a common mechanism. FEMS Microbial Rev 34, 1076-1112.
Rose, T., Sebo, P., Bellalou, J. , and Ladant, D. (1995) Interaction of calcium with Bordetella pertussis adenylate cyclase toxin. Characterization of multiple calcium-binding sites and calcium-induced conformational changes. J Biol Chem 270, 26370-26376.
Sotomayor-Perez, A. C., Subrini, O., Hessel, A., Ladant, D., and Chenal, A. (2013) Molecular Crowding Stabilizes Both the Intrinsically Disordered Calci um-Free State and the Folded Calci um-Bound State of a Repeat in Toxin (RTX).
Baumann, U., Wu, S., Flaherty, K. M., and McKay, D. B. (1993) Three-dimensional structure of the alkaline protease of Pseudomonas aeruginosa: a two-domain protein with a calcium binding parallel beta roll motif. EMBO J 12, 3357-3364.
Meier, R., Drepper, T., Svensson, V., Jaeger, K. E., and Baumann, U. (2007) A calcium-gated lid and a large beta-roll sandwich are revealed by the crystal structure of extracellular lipase from Serratia marcescens. J Biol Chem 282, 31477-31483.
Satchell, K. J. (2011) Structure and function of MARTX toxins and other large repetitive RTX proteins. Annual review of microbiology 65, 71-90.
Masure, H. R., Au, D. C., Gross, M. K. , Donovan, M. G., and Storm, D. R. (1990) Secretion of the Bordetella pertussis adenylate cyclase from *Escherichia coli* containing the hemolysin operon. Biochemistry 29, 140-145.
Guermonprez, P., Khelef, N., Blouin, E., Rieu, P., Ric ciar di-Cast agnoli, P., Guise, N., Ladant, D., and Leclerc, C. (2001) The adenylate cyclase toxin of Bordetella pertussis binds to target cells via the alpha(M)beta(2) integrin (CD11b/CD18). J Exp Med 193, 1035-1044.
Rogel, A., and Hanski, E. (1992) Distinct steps in the penetration of adenylate cyclase toxin of Bordetella pertussis into sheep erythrocytes. Translocation of the toxin across the membrane. J Biol Chem 267, 22599-22605.
Paccani, S. R., Finetti, F., Davi, M., Patrussi, L., D'Elios, M. M., Ladant, D., and Bal dari, C. T. (2011) The Bordetella pertussis adenylate cyclase toxin binds to T cells via LFA-1 and induces its disengagement from the immune synapse. J Exp Med 208, 1317-1330.
Guermonprez, P., Ladant, D., Karimova, G., Ullmann, A., and Leclerc, C. (1999) Direct delivery of the Bordetella pertussis adenylate cyclase toxin to the MHC class I antigen presentation pathway. J Immunol 162, 1910-1916.
Gordon, V. M., Young, W. W., J r., Lechler, S. M., Gray, M. C. , Leppla, S. H . , and Hewlett, E. L. (1989) Adenylate cyclase toxins from Bacillus anthracis and Bordetella pertussis. Different processes for interaction with and entry into target cells. J Biol Chem 264, 14792-14796.
Rogel, A. , Schultz, J. E., Brownlie, R. M. , Coote, J. G., Parton, R. , and Hanski, E. (1989) Bordetella pertussis adenylate cyclase: purification and characterization of the toxic form of the enzyme. Embo J 8, 2755-2760.
Veneziano, R., Rossi, C., Chenal, A., Devoisselle, J. M., Ladant, D., and Chopineau, J. (2013) Bordetella pertussis adenylate cyclase toxin translocation across a tethered lipid bilayer. Proc Natl Acad Sci US A 110, 20473-20478.
Uribe, K. B., Etxebarria, A. , Martin, C., and Ostolaza, H. (2013) Ca lpain-Mediated Processing of Adenylate Cyclase Toxin Generates a Cytosolic Soluble Catalytically Active N-Terminal Domain. PLoS One 8, e67648.
Heveker, N. , and Ladant, D. (1997) Characterization of mutant Bordetella pertussis adenylate cyclase toxins with reduced affinity for calmodulin. Implications for the mechanism of toxin entry into target cells. European journal of biochemistry I FEBS 243, 643-649.
Benz, R. , Maier, E., Ladant, D., Ullmann, A., and Sebo, P. (1994) Adenylate cyclase toxin (CyaA) of Bordetella pertussis. Evidence for the formation of small ion-permeable channels and comparison with HIyA of *Escherichia coli*. J Biol Chem 269, 27231-27239.
Hewlett, E. L., Donato, G. M., and Gray, M. C. (2006) Macrophage cytotoxicity produced by adenylate cyclase toxin from Bordetella pertussis: more than just making cyclic AMP! Molecular microbiology 59, 447-459.
Gentile, F., ,Knipling, L. G., Sackett, D. L., and Wolff, J. (1990) Invasive adenylyl cyclase of Bordetella pertussis. Physical, catalytic, and toxic properties. J Biol Chem 265, 10686-10692.
Hewlett, E. L., Urban, M. A., Manclark, C. R., and Wolff, J. (1976) Extracytoplasmic adenylate cyclase of Bordetella pertussis. Proc Natl Acad Sci U S A 73, 1926-1930.
Sebo, P., Glaser, P., Sakamoto, H., and Ullmann, A. (1991) High-level synthesis of active adenylate cyclase toxin of Bordetella pertussis in a reconstructed *Escherichia coli* system. Gene 104, 19-24.
Dadaglio, G., Morel, S., Bauche, C., Moukrim, Z., Lemonnier, F. A. , Van Den Eynde, B. J., Ladant, D., and Leclerc, C. (2003) Recombinant adenylate cyclase toxin of Bordetella pertussis induces cytotoxic T lymphocyte responses against HLA*0201-restricted melanoma epitopes. Int Immunol 15, 1423-1430.
Preville, X., Ladant, D., Timmerman, B., and Leclerc, C. (2005) Eradication of established tumors by vaccination with recombinant Bordetella pertussis adenylate cyclase carrying the human papillomavirus 16 E7 oncoprot ein. Cancer Res 65, 641-649.
Saran, M. F., Fayolle, C., Sebo, P., Ladant, D., Ullmann, A., and Leclerc, C. (1997) Anti-viral protection conferred by recombinant adenylate cyclase toxins from Bordetella pertussis carrying a CD8+ T cell epitope from lymphocytic choriomeningitis virus. Proc Natl Acad Sci USA 94, 3314-3319.
Welch, R. A. (1991) Pore-forming cytolysins of gram-negative bacteria. Molecular microbiology 5, 521-528.
El-Azami-El-Idrissi M. et al., Interaction of Bordetella pertussis Adenylate Cyclase with CD11b/CD18, J. Biol. Chem. Oct. 3, 2003; 278(40):38514-21.
Needleman and Wunsch. A General Method Applicable to the Search for Similarities in the Amino Acid Sequence of Two Proteins, J.Mol. Biol. 48,443-453, 1970.
Guiso et al, Bordetella adenylate cyclase is a virulence associated factor and an immunoprotective antigen, Microbial pathogenesis 1989, 7(5):373-80.
J. C. Karst et al: "Calcium, Acylation, and Molecular Confinement Favor Folding of Bordetella pertussis Adenylate Cyclase CyaAToxin into a Monomericand Cytotoxic Form" Journal of Biological Chemistry vol. 289, No. 44, Sep. 17, 2014 (Sep. 17, 2014), pp. 30702-3071.
Khosravani et al: "Formulation of the adenylate cyclase toxin of Bordetella pertussis as protein-coated microcrystals", Vaccine Elsevier Ltd, GB, vol. 25, No. 22, May 6, 2007 (May 6, 2007), pp. 4361-4367.

(56) References Cited

OTHER PUBLICATIONS

A Rogel et al: "Bordetella pertussis adenylate cyclase: purification and characterization of the toxic form of the enzyme", The EMBO journal,Sep. 1, 1989 (Sep. 1, 1989), pp. 2755-2760.
Ana-Ciristina Sotomayor-Perez: "Molecular Crowding Stabilizes Both the Intrinsically Disordered Calcium-Free State and the Folded Calcium-Bound State of a Repeat in Toxin (RTX)Protein" Ojournal of the American Chemical Socieity, vol. 135, No. 32, Aug. 14, 2013 (Aug. 14, 2013), pp. 11929-1193.
Perez A C S, et al: "Characterization of the Regions Involved in the Calcium-Induced Folding of the Intrinsically Disordered RTX Motifs from the Bordetella pertussis Adenylate Cyclase Toxin" Journal of Molecular Biology, Academic Press, United Kingdom, vol. 397, No. 2, Mar. 26, 2010 (Mar. 26, 2010), pp. 534-549.
Westrop G D et al: "Bordetella pertussis adenylate cyclase toxin: proCyaA and CyaC proteins synthesised separately in *Escherichia coli* produce active toxin in vitro", Gene, Elsevier, Amsterdam, NL, vol. 180, No. 1-2, Nov. 21, 1996 (Nov. 21, 1996), pp. 91-99.
Huan-Xiang Zhou et al: "Macromolecular Crowding and Confinement: Biochemical, Biophysical, and Potential Physiological Consequences" Annual Review of Biophysics, vol. 37, No. 1, Jun. 1, 2008 (Jun. 1, 2008), pp. 375-397.
International Search Report for PCT/EP2015/066494, dated Oct. 9, 2015.

\* cited by examiner

A

B

C

D

MONOMERIC AND FUNCTIONAL ADENYLATE CYCLASE CYAA TOXIN

BACKGROUND OF THE INVENTION

The adenylate cyclase toxin (hereafter referred to as the "CyaA toxin") produced by *Bordetella pertussis*, the causative agent of whooping cough, is one of the major virulence factors of this organism (12,13). CyaA plays an important role in the early stages of respiratory tract colonization by *B. pertussis*. CyaA is able to invade eukaryotic target cells, where it is activated by an endogenous protein, calmodulin (CaM), and produces high levels of cAMP that, in turn, alters the cellular physiology.

CyaA is a 1706-residue long protein organized in a modular fashion. The ATP-cyclizing, CaM-activated, catalytic domain (ACD) is located in the 400 amino-terminal residues (6) while the carboxy-terminal 1306 residues are responsible for the hemolytic phenotype of *B. pertussis* (16). Both activities can function independently as adenylate cyclase and haemolysin, respectively. Several domains can be identified in the hemolytic region. The so-called translocation region, spanning residues 400 to 500, is crucial for the translocation of ACD across the plasma membrane (11) and exhibits properties related to membrane-active peptides (17). The hydrophobic region, spanning residues 500 to 750, contains several hydrophobic segments predicted to adopt alpha-helical structures. The acylation region, spanning residues 800 to 1000, contains two post-translational modification sites that are essential for the cytotoxic activities of CyaA (19). The toxin is indeed synthesized as an inactive precursor, proCyaA that is converted into the active CyaA toxin upon specific acylation of Lys 860 and Lys 983 by a dedicated acyltransferase, CyaC (19). The C-terminal part of CyaA is the cell receptor-binding domain (RD, residues 1000 to 1706). This domain consists of ~40 copies of a calcium-binding, glycine and aspartate-rich nonapeptide repeat that is characteristic of a large family of bacterial cytolysins known as RTX (Repeat-in-ToXin) toxins (22,23). These motifs constitute the main $Ca^{2+}$ binding sites of the protein (24). The RTX motifs are intrinsically disordered in the absence of calcium (8, 26) and fold, in the presence of calcium, into a structure called β-roll as revealed in the three-dimensional structures of several RTX proteins (27). CyaA is secreted across the bacterial envelope by a dedicated type I secretion machinery made of CyaB, CyaD, and CyaE (15,30). Once secreted, CyaA binds in a calcium-dependent manner to the CD11b/CD18 integrin expressed on myeloid cells, such as macrophages, neutrophils, dendritic cells, and natural killer cells that are the primary targets of this toxin in vivo (31). Yet, CyaA can also efficiently intoxicate a variety of cell types lacking this receptor (24,32,35).

One of the main originalities of CyaA, with respect to other bacterial or plant toxins, stems from its unique mechanism of penetration into eukaryotic cells: CyaA is the only known toxin able to translocate its catalytic domain directly across the plasma membrane of the targeted cells, from the extra-cellular side into the cytosol (36,40,41). The molecular mechanism by which CyaA enters into target cells remains, however, largely unknown. It is believed that after binding via the RD domain to the CD11b/CD18 receptor, the hydrophobic regions of CyaA may insert into the plasma membrane of target cells. The catalytic domain is then delivered through the plasma membrane, possibly through a transient and local destabilization of the membrane integrity (11,17, 42,43) to reach the cytosol, where upon binding to the endogenous CaM, its enzymatic activity is stimulated to generate supra physiologic levels of cAMP (41,44). Moreover, CyaA, after insertion into the membrane, can also form cation-selective pores, which impair membrane impermeability and ultimately cause cell lysis (45). This membrane damaging activity is thought to synergize with the cAMP intoxication ability thus increasing the overall cytotoxicity of the toxin (47).

Since its original description in the early eighties, numerous reports have highlighted the heterogeneity of the molecular forms of this toxin that appeared to be prone to aggregation into multimeric non-functional complexes (41, 49,51). As a matter of fact, the CyaA toxin exhibits a pronounced hydrophobic character due to post-translational acylations and the presence of a hydrophobic domain that drastically limits its solubility.

Due to these characteristics, CyaA has been mostly extracted, purified and stored in the presence of high concentration of chaotropic agent (usually urea) to prevent its aggregation. In initial works, CyaA was purified from urea extracts from wild-type *B. pertussis* bacteria (49, 52). Later, after cloning of the cyaA gene in the late eighties, CyaA has been largely produced as a recombinant protein in *E. coli*, also co-expressing CyaC to permit its post-translational acylation (2,53). In these recombinant cells, CyaA mainly accumulates as inclusion bodies requiring denaturing conditions for its solubilization. In most of these studies, the protein batches were stored after purification in buffers containing urea (higher than 6 M) to maintain it in a soluble form. The cytotoxic activities of CyaA have been usually tested by directly diluting the stock solution of toxin into cell suspensions without taking special care about its refolding process and/or its final oligomeric status. Even biological assays of CyaA or derivatives like CyaA-based vaccines (54-56) in animals have been carried out with recombinant CyaA toxoid preparations that were extemporaneously diluted in physiological buffers just before administration.

So far, the use of a chaotropic agent such as urea was thought to be the only means to prevent CyaA aggregation and preserve its solubility upon purification and storage. Yet, two major drawbacks result from the maintenance in denaturing conditions. First, it is not possible to combine CyaA with other antigens in a vaccine, since the latter may be destabilized in the presence of the chaotropic agent. Second, the present inventors herein show that the required dilution of the CyaA toxins in physiological buffers leads to enhance the proportion of non-fonctional multimers in the solution to be injected. As a matter of fact, refolding of the CyaA toxin upon urea removal either through dialysis, dilution or rapid buffer exchange on desalting column, indicated that in all these conditions CyaA mainly formed multimers, from tetramers to higher order oligomers, as reported earlier (41,49).

To solve these two problems, the present inventors aimed to identify conditions that might favor the refolding of CyaA in a functional and non-aggregated form, in the absence of urea.

By doing so, they found that refolding of urea-unfolded CyaA under molecular confinement (e.g., by size-exclusion chromatography on resin/gels with small particle and pore sizes) resulted in a significant fraction of the molecules eluting as a monomeric species. Importantly, the folding of CyaA into a monomeric form was critically dependent upon the presence of calcium as well as on the post-translational acylation of the protein.

Moreover, the present inventors show that, although the secondary structure content of the monomeric and multimeric species is rather similar, the monomeric form of CyaA displayed significantly higher functional activities than the multimeric ones.

The present application therefore discloses new experimental conditions enabling to retrieve recombinant CyaA toxin that i) exhibits better biological properties than the ones currently used in immunotherapy or whooping cough vaccination, and that ii) is stable in a buffer in the absence of any urea denaturant.

FIGURE LEGENDS

FIG. 1: CyaA refolding followed by fluorescence and circular dichroism. Refolding of urea-denatured apo-CyaA (open circles) or holo-CyaA (black circles) followed by (A) tryptophan intrinsic fluorescence, (B) ANS fluorescence and (C and D) CD in the far-UV region. Maximum emission wavelength values are reported for both tryptophan and ANS fluorescence. (C) Far-UV CD spectra of CyaA (1 µM) in the absence (dashed line) and in the presence (full line) of 2 mM calcium are shown in the presence of 6 M urea and after extensive dialysis against buffer A or buffer B. Changes of mean residual ellipticity (MRE) of the n-π* band followed at 220 nm are shown in panel D. For all spectra and MRE changes, the contributions from the buffer were subtracted.

Figure 2:
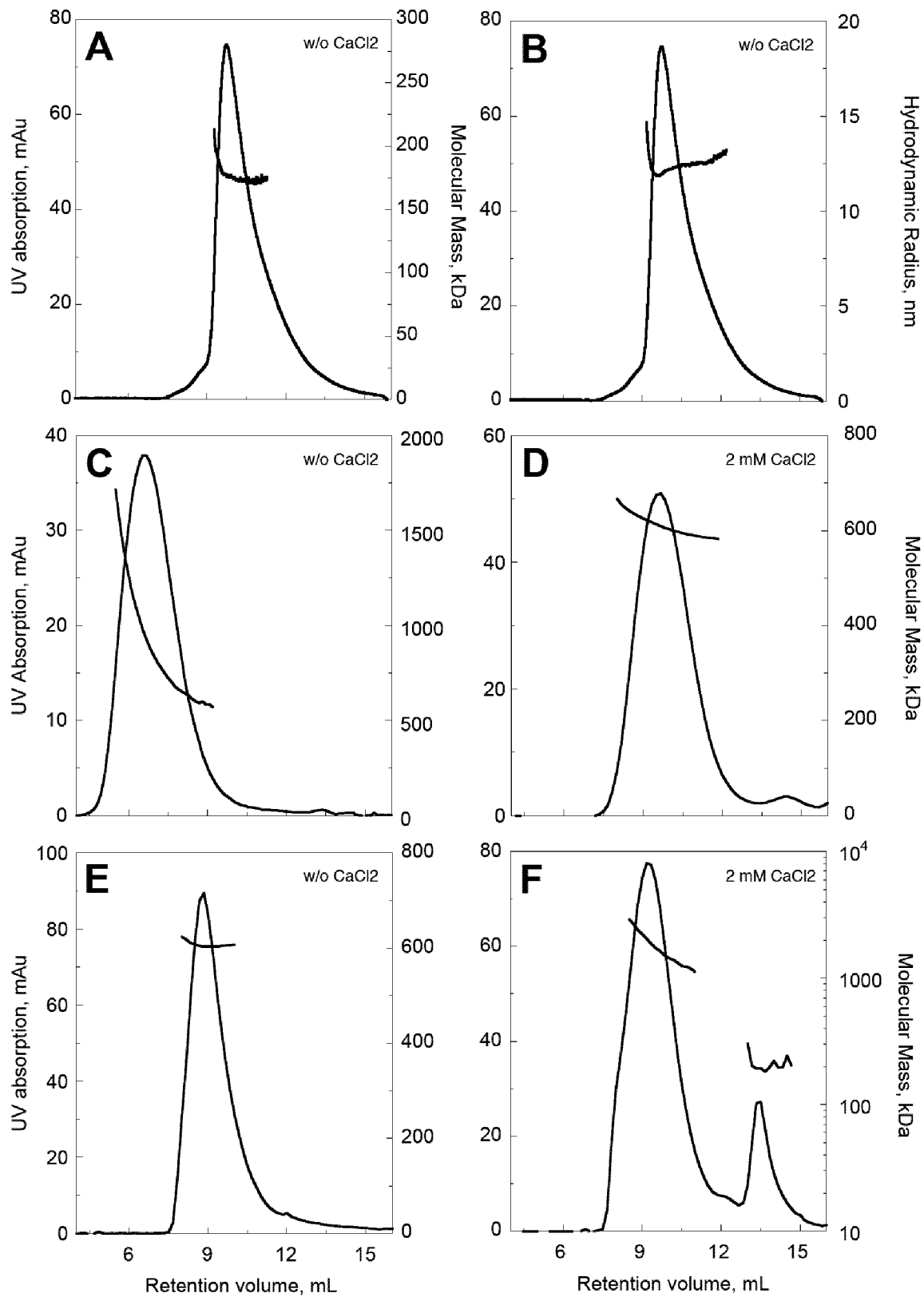

FIG. 2: Size exclusion chromatography of CyaA in the presence and in the absence of urea after dialysis or desalting. (A-B): Size exclusion chromatography (SEC) of CyaA on TSK 4000SWxl column equilibrated in 4 M urea in buffer A (without calcium) with the molecular mass (A) and hydrodynamic radius (B) distributions measured by tetra detector array (TDA). (C—F): SEC analysis on the TSK 4000SWxl column of CyaA samples after dialysis on Float-A-Lyzer G2 against buffer A (panel C) or buffer B (panel D), or after CyaA desalting on G25SF in buffer A (panel E) or buffer B (panel F).

Figure 3:
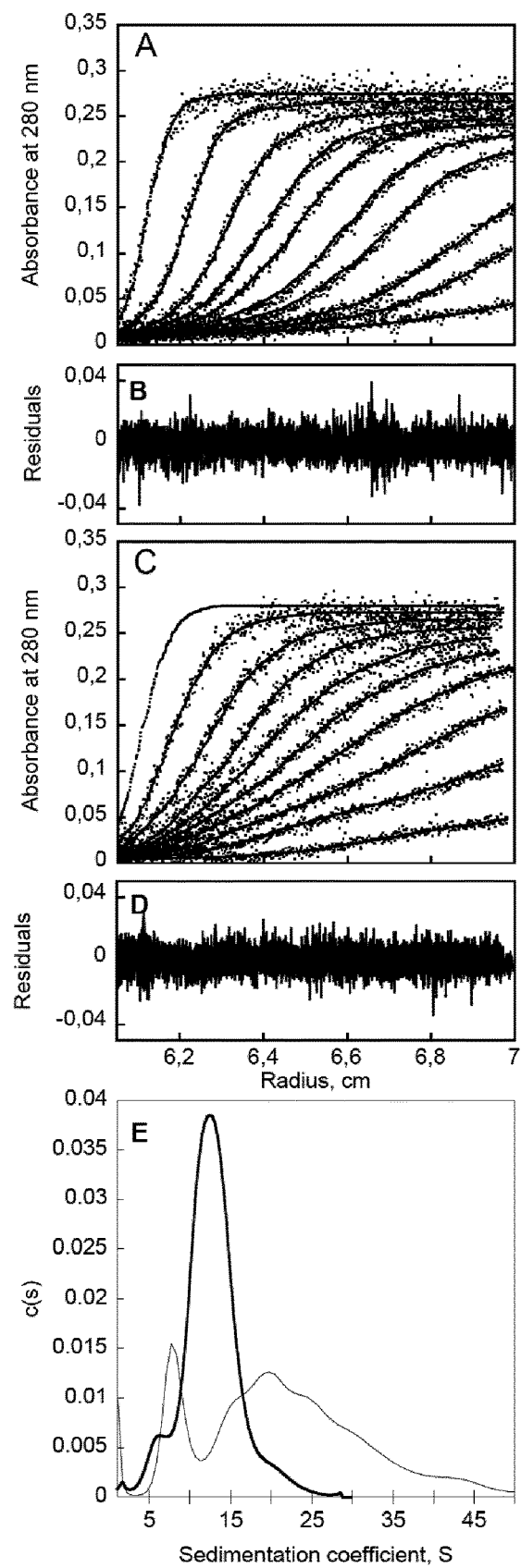

FIG. 3: Analytical ultracentrifugation of CyaA after urea removal by desalting on G25. CyaA (in 8 M urea) was chromatographed on G25SF equilibrated in buffer A or buffer B. The sedimentation distribution profile of CyaA (1.4 µM) was analyzed with a Beckman-Coulter XL-I analytical ultracentrifuge using an AnTi rotor. Experimental data of sedimentation velocity (dots) in the absence (A) and in the presence (C) of 2 mM calcium were fitted with the Lamm equation (lines) and the distributions of the residual values are shown in panel (B) and (D) respectively. (E) Sedimentation coefficient distribution of apo-CyaA (dashed line), and holo-CyaA (thick line) deduced from the fitted curves.

Figure 4:
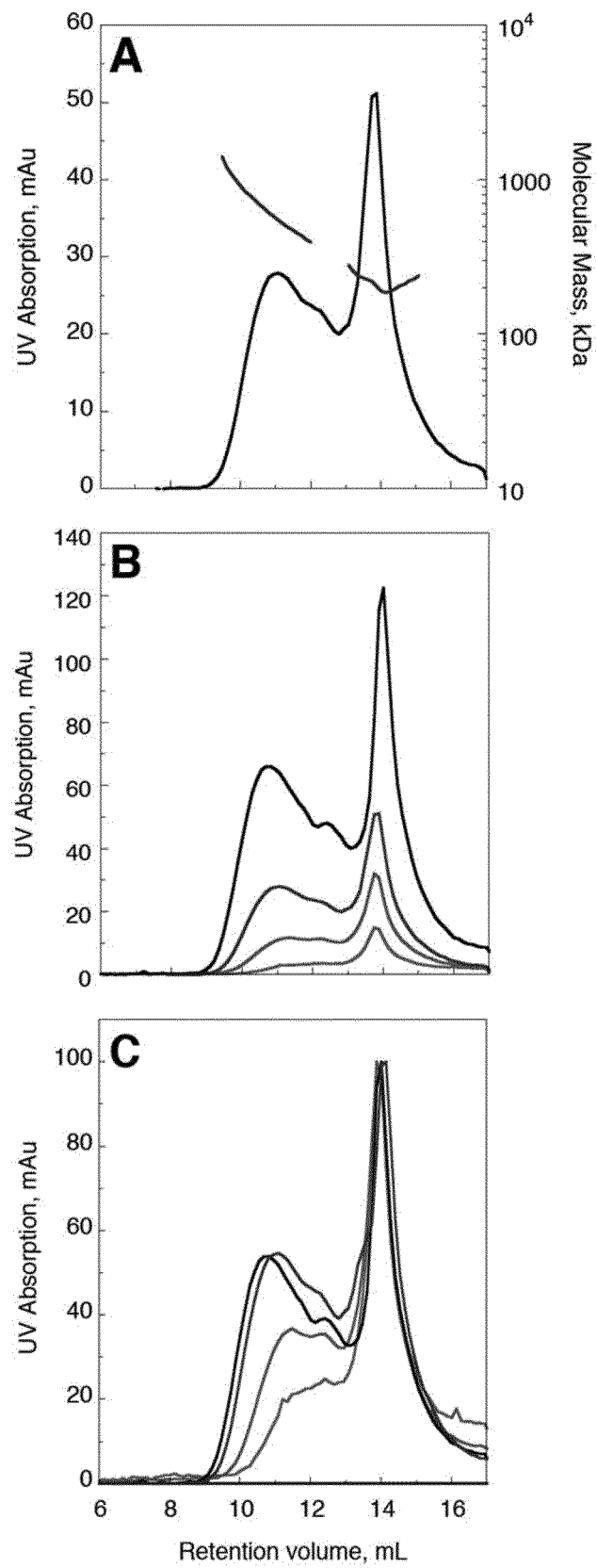

FIG. 4: Refolding of CyaA monomers by SEC-TDA. (A) SEC-TDA analysis of CyaA (5 µM in 8M urea) directly injected on a TSK 4000SWxl column equilibrated in buffer B (with 2 mM calcium). UV profile and molecular mass distribution are shown. (B) SEC-TDA in same conditions of CyaA (in 8M urea) loaded at the following concentrations from bottom to top: 1 µM; 2.5 µM; 5 µM; 12 µM. (C) The UV profiles shown in B are normalized to the monomer peak (≈14 mL) intensity to highlight the concentration-dependent distribution of monomers and multimers.

Figure 5:
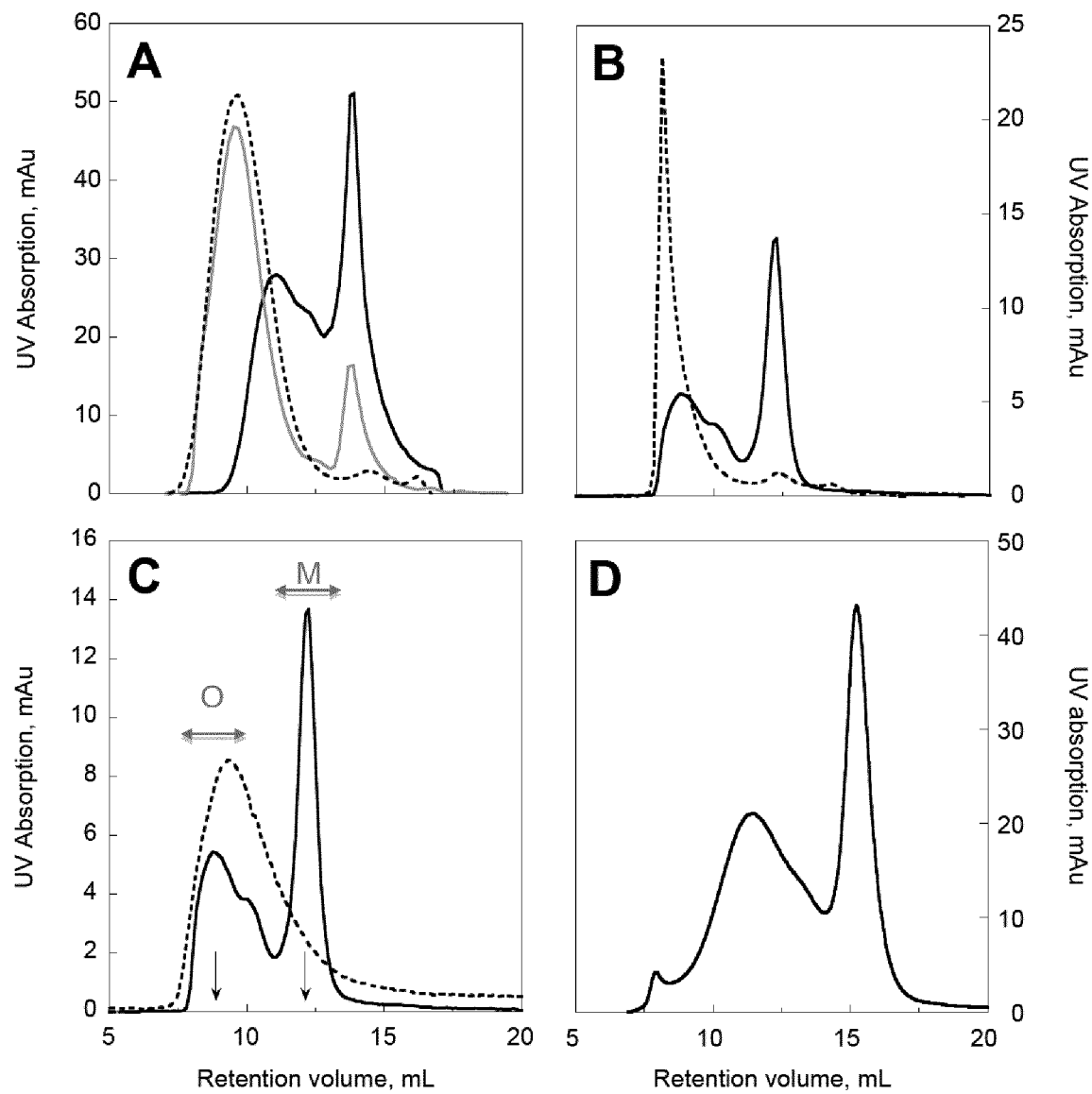

FIG. 5: Molecular confinement favors CyaA folding into monomeric species. (A) SEC of CyaA on TSK 4000SWxl (particle size: 8 µm) after urea removal by dialysis (dashed), desalting on G25SF (thin grey) and direct refolding on TSK 4000SWxl (bold trace). (B) SEC of CyaA on Superdex200 10/300 after urea removal by dialysis (dashed) and by direct refolding (bold trace) on the column. (C) SEC of CyaA directly loaded on Superdex200 10/300 (bold trace; particle size: 11±2 µm) or on Sephacryl S200 (dashed trace; particle size: 50±25 µm). Both columns had a bed volume of 24 mL. (D) SEC of CyaA loaded on Superose 6HR (particle size: 13±2 µm; total volume of 24 ml). Samples of 200 L of 5 µM CyaA in 8 M urea, 20 mM Hepes, pH 7.5 were loaded in all experiments. All SEC were carried out in buffer B.

Figure 6:
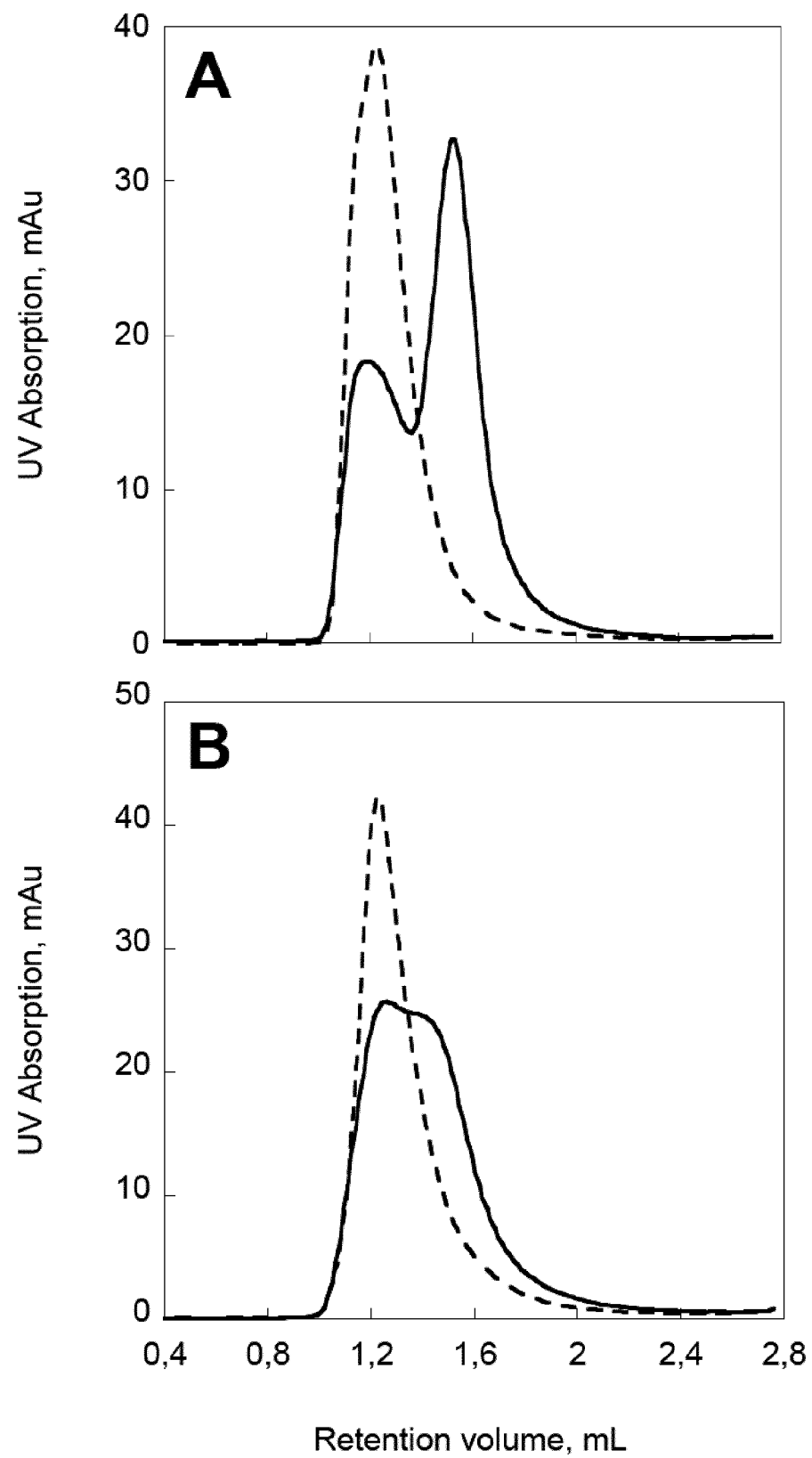

FIG. 6: Post-translational acylation of CyaA and calcium binding are required to produce CyaA monomers. SEC of CyaA (A) and proCyaA (B) refolded on Superdex S200 5/150 in the absence (dashed traces, buffer A) and in the presence (thick traces, buffer B) of 2 mM calcium. Samples of 50 µL of 5 µM CyaA or proCyaA (in 8 M urea, 20 mM Hepes, pH 7.4) were loaded in each experiment.

Figure 7:
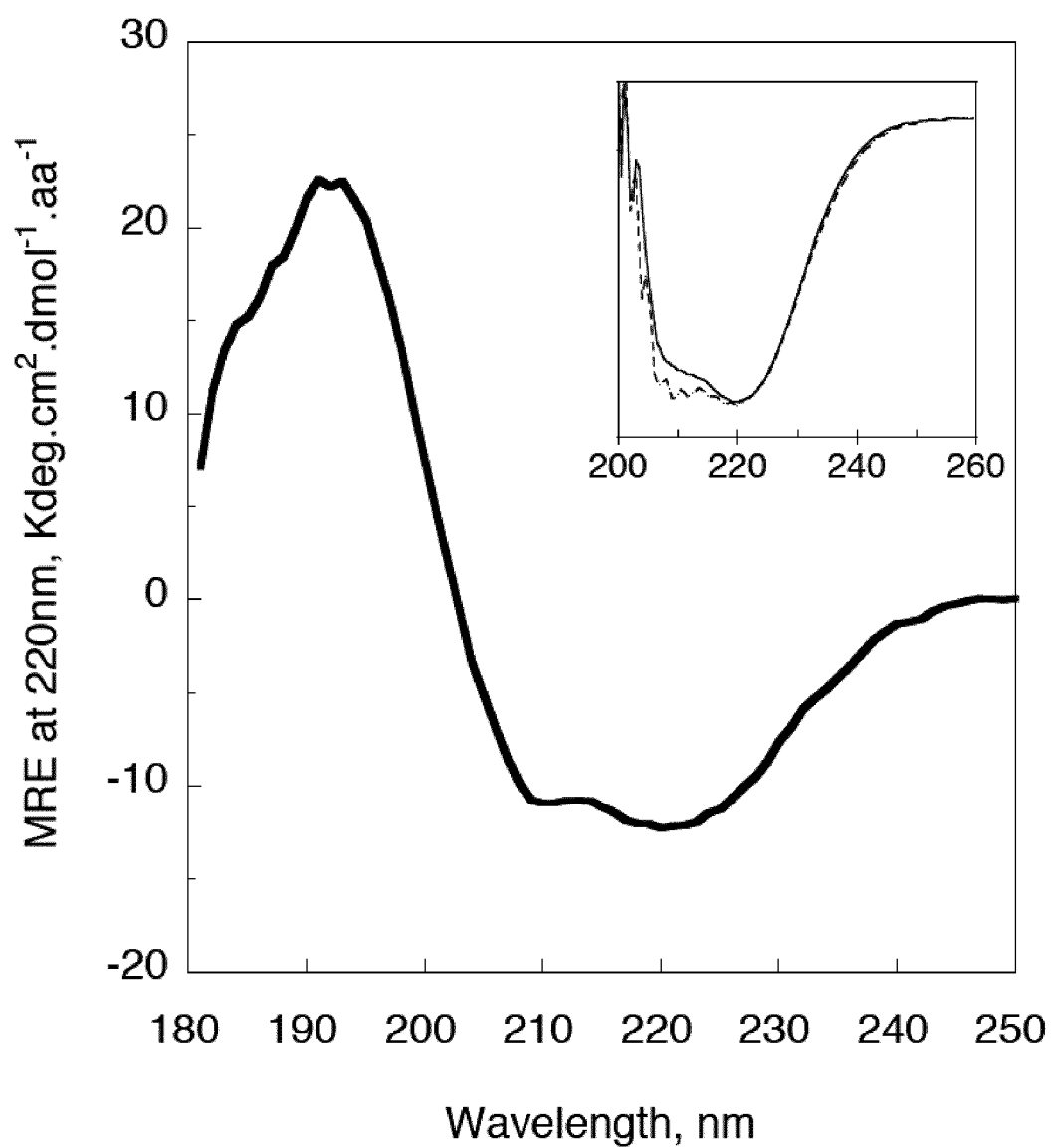

FIG. 7: Synchrotron Radiation Circular dichroism in the far-UV region of holo-CyaA. Far-UV SR-CD spectra of holo-CyaA monomers in 20 mM Hepes, 150 mM NaCl, 2 mM CaCl2, pH 7.4. Deconvolution by K2D3 provides the following secondary structure content prediction: 24% of helix and 27% of beta-sheets. Inset: comparison between far-UV CD spectra of monomers and multimers of CyaA acquired on an Aviv spectropolarimeter, showing that n-π* bands of both species exhibit similar intensities.

Figure 8:
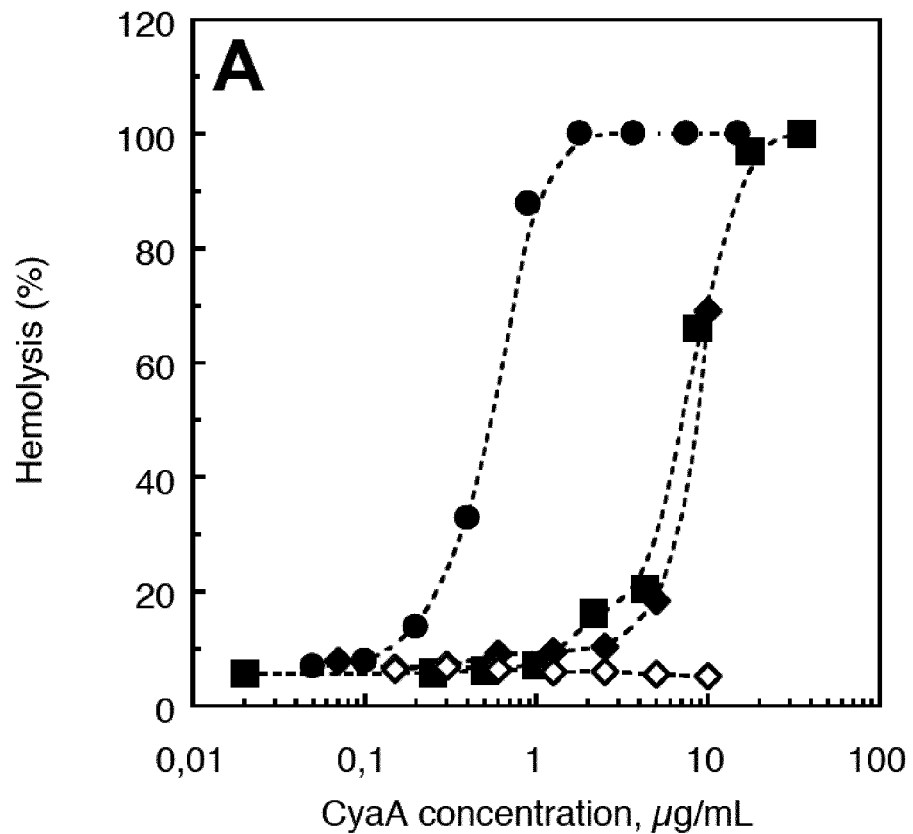
Figure 8:
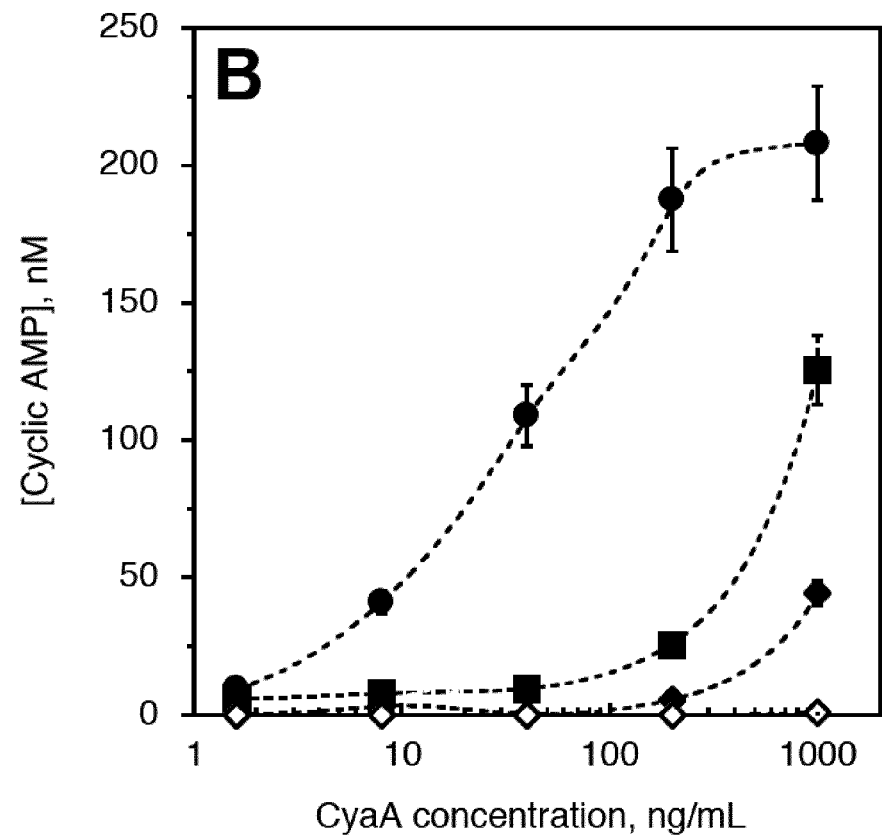

FIG. 8: Hemolytic and cAMP-inducing activities of the various CyaA preparations. The different CyaA samples, i.e., CyaA renatured by G25 buffer exchange in the presence of calcium (black diamond), CyaA renatured by G25 buffer exchange in the absence of calcium (open diamond), the oligomeric (black square) and monomeric (black circle) CyaA species collected after refolding on TSK column in the presence of calcium, were directly diluted into erythrocytes suspension (5×108 cells/ml in buffer B) to reach the indicated final concentrations. All hemolysis experiments were performed in the presence of 2 mM calcium, excepted the G25 buffer exchanged-CyaA in the absence of calcium that was tested in the presence of 4 mM EDTA.

Figure 9:
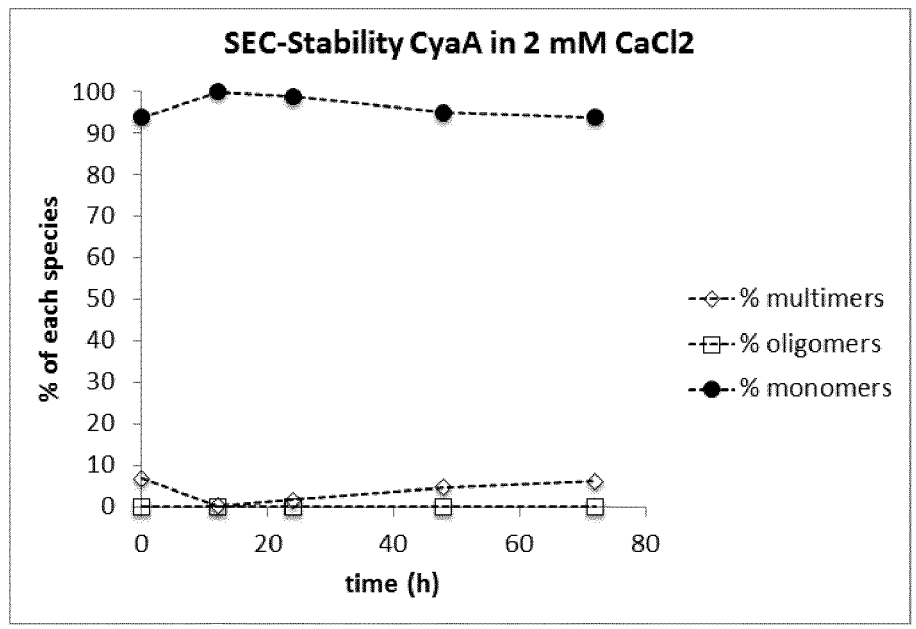
Figure 9:
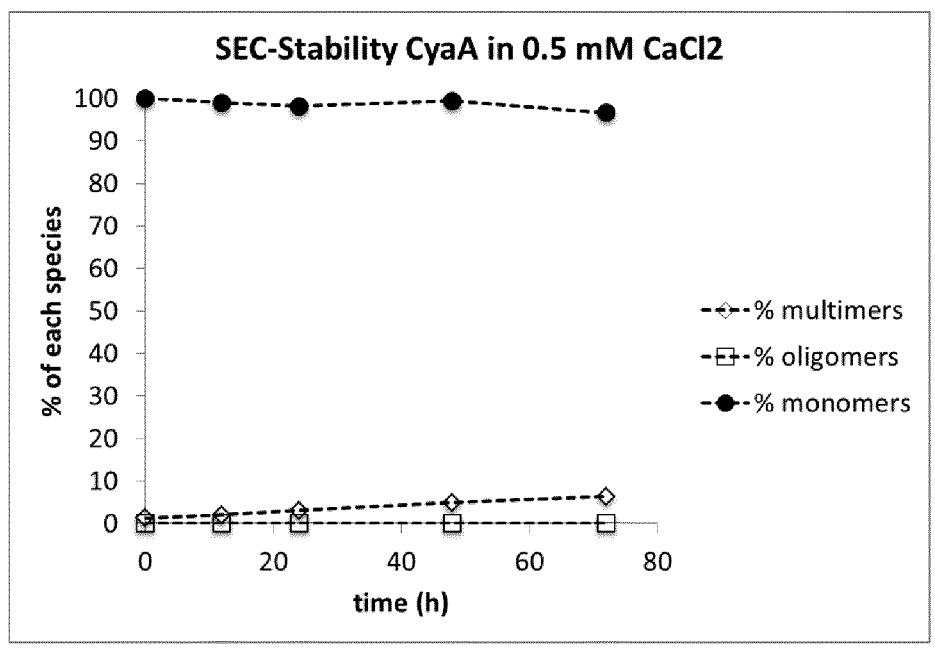
Figure 9:
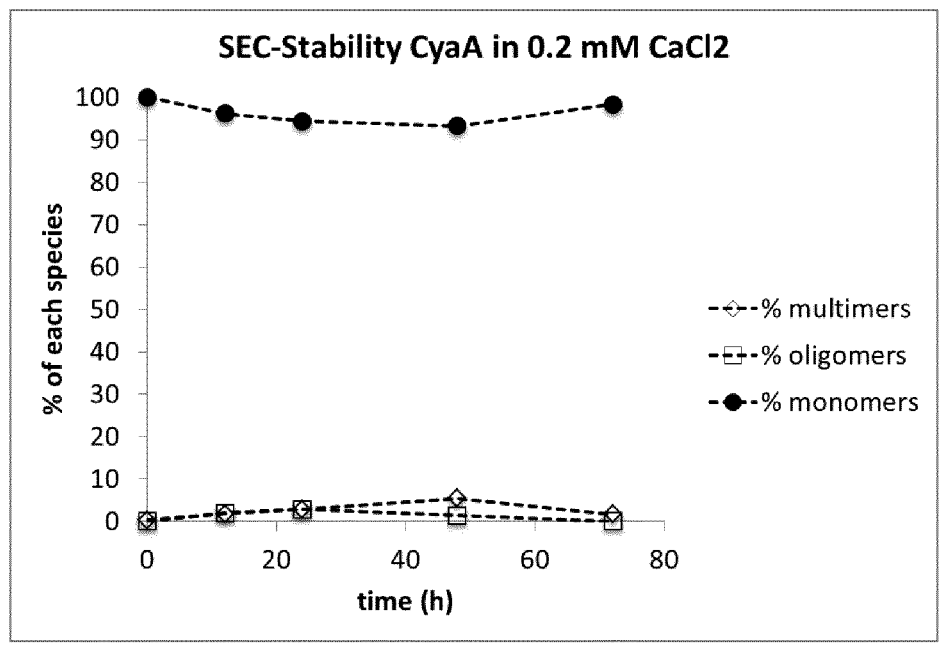
Figure 9:
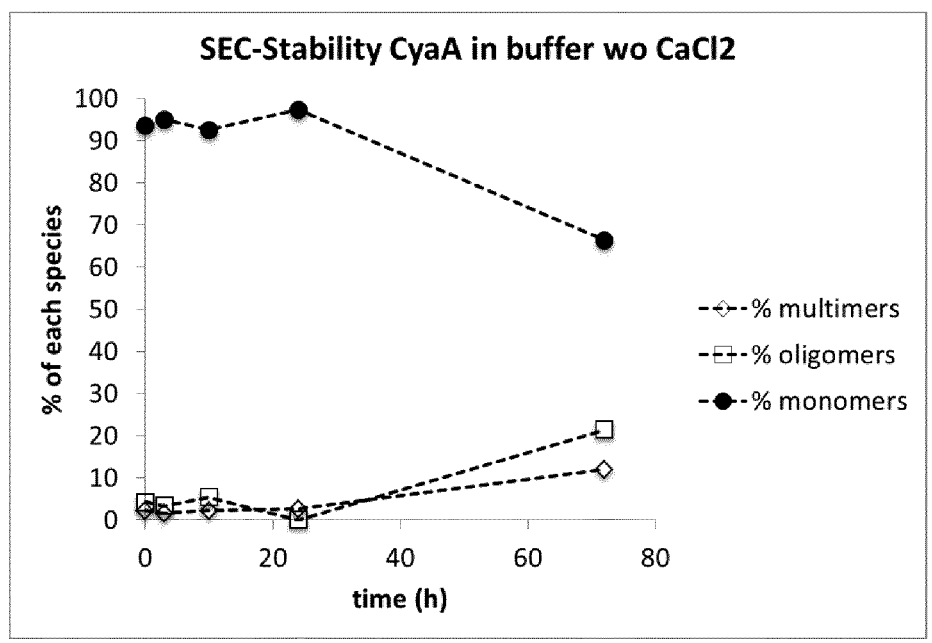

FIG. 9: Stability of hCyaAm over time followed by Size Exclusion Chromatography. Proportion of multimers, oligomers and monomers in a sample of hCyaAm at 25° C. in the presence of various concentrations of calcium in the buffer (A=2 mM $CaCl_2$, B=0.5 mL $CaCl_2$, C=0.2 mM $CaCl_2$, and D=without $CaCl_2$), as a function of time.

Figure 10:
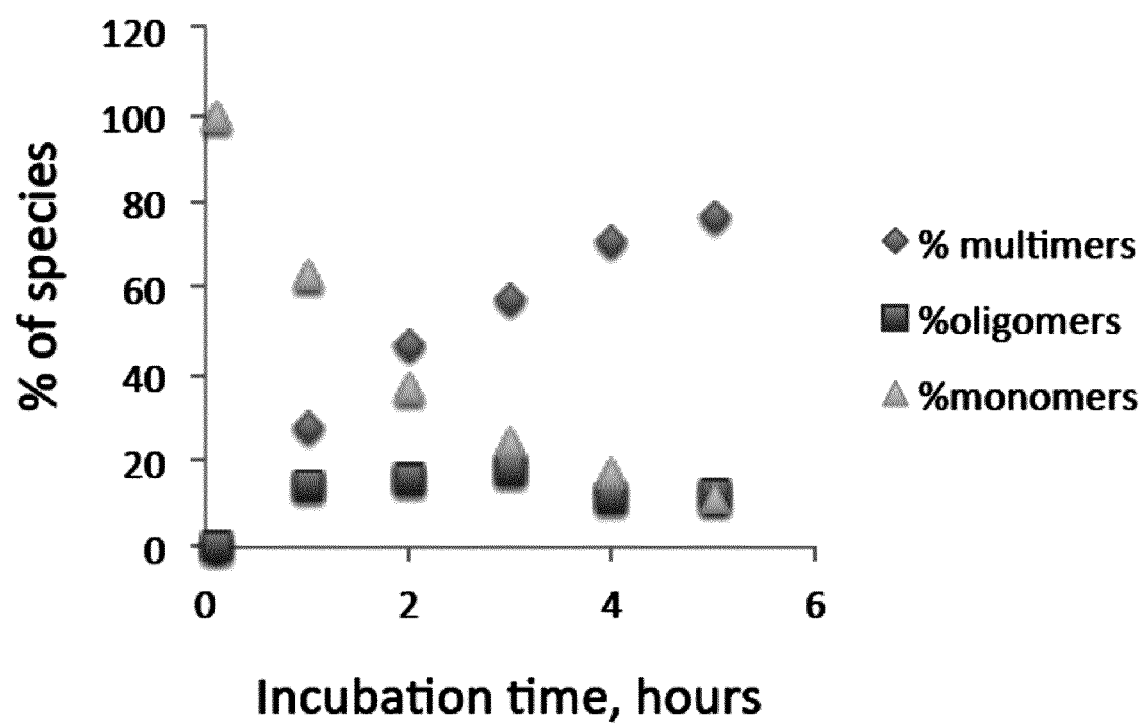

FIG. 10: Stability of hCyaAm in the presence of EDTA over time followed by Size Exclusion Chromatography. Proportion of multimers, oligomers and monomers in a sample of hCyaAm at 25° C. in the presence of 0.2 mM of EDTA as a function of time.

Figure 11:
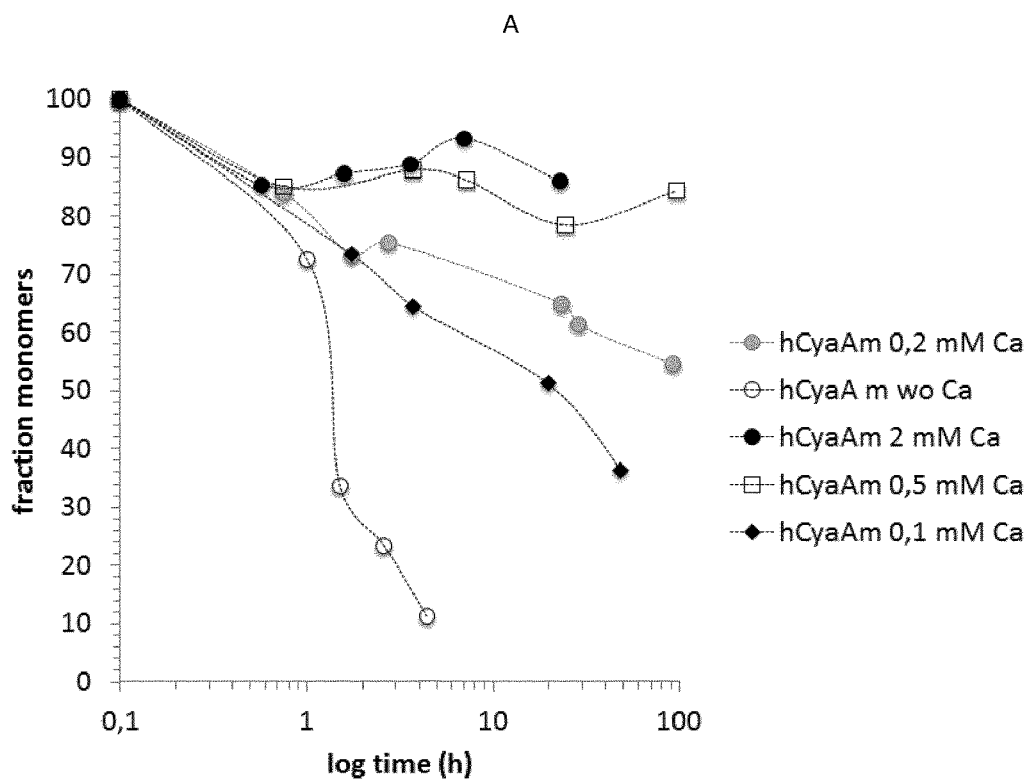
Figure 11:
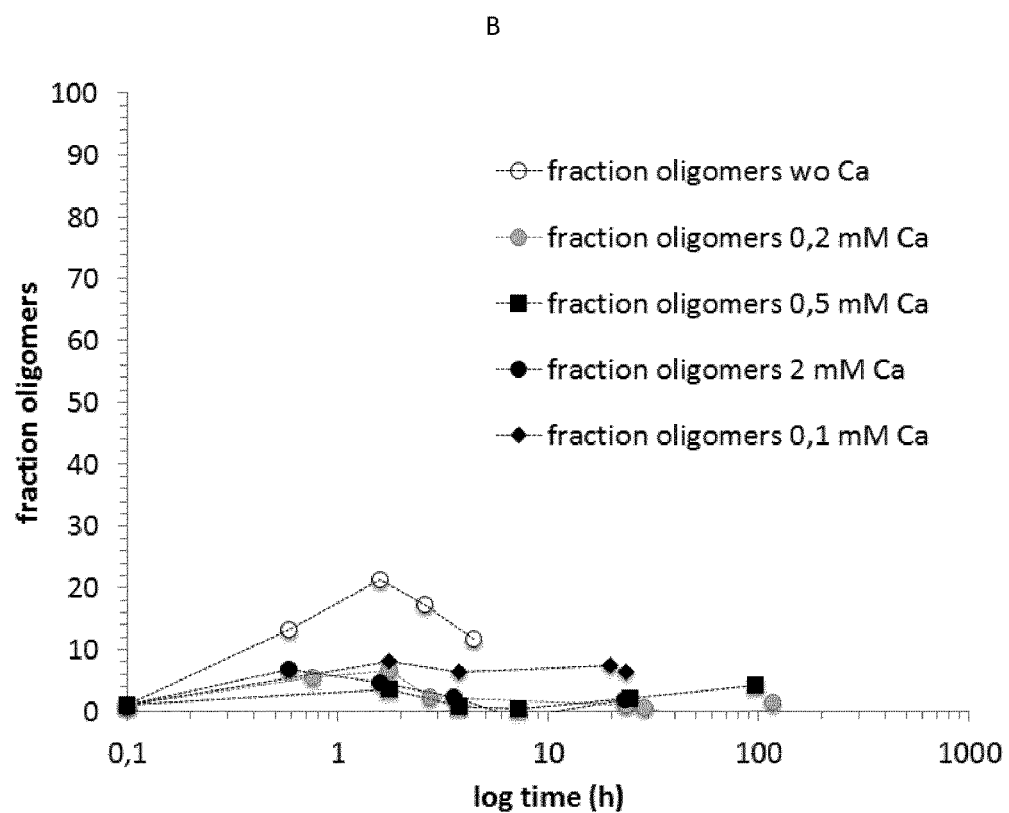
Figure 11:
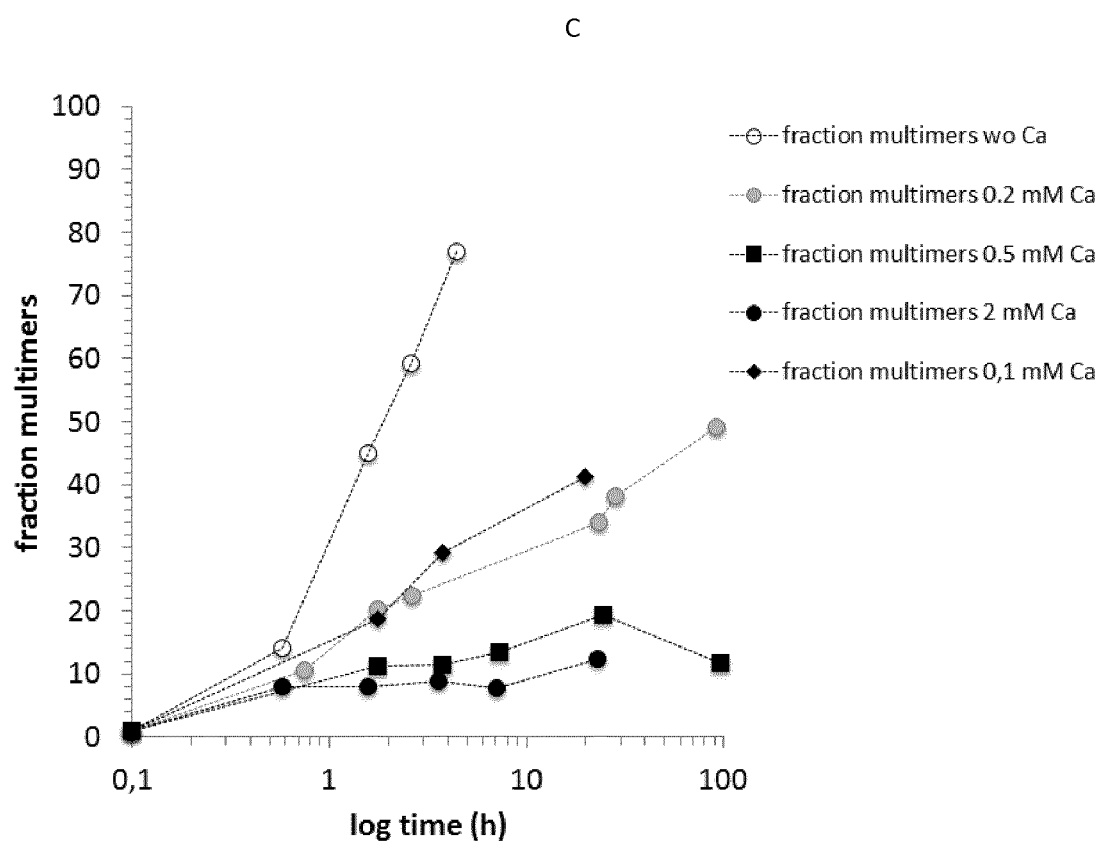

FIG. 11: Stability of hCyaA-OVAm in the presence of Ca over time followed by Size Exclusion Chromatography. Proportion of multimers (C), oligomers (B) and monomers (A) in a sample of hCyaA-OVAm at 25° C. in the presence of various concentrations of calcium in the buffer (0, 0.2 mM, 2 mM, 0.5 mM, 0.1 mM), as a function of time.

Figure 12:
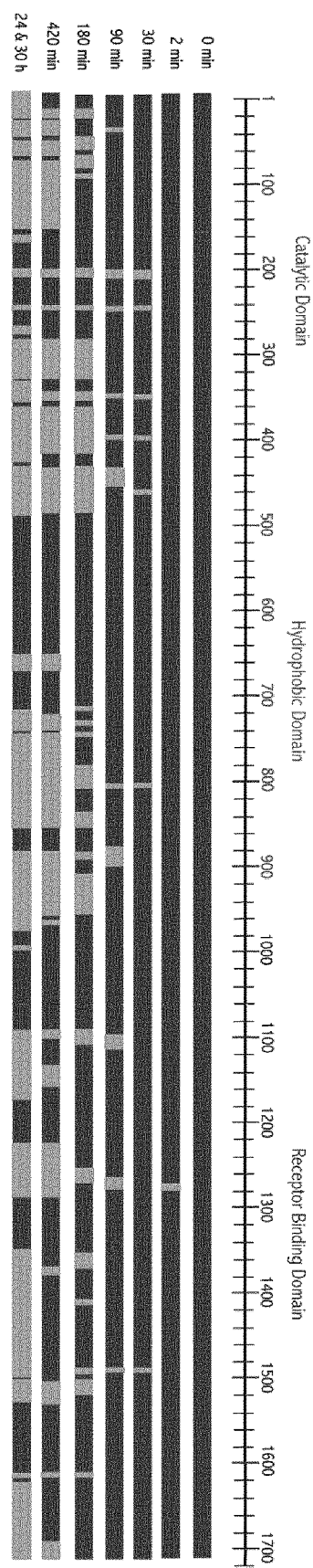

FIG. 12: MS analysis of limited proteolysis of hCyaAm in the presence of 2 mM calcium. Proteolysis of hCyaAm was done at a trypsin:CyaA ratio of 1:40 in the presence of 2 mM CaCl2 and quenched at various time points by AEBSF and frozen into liquid nitrogen.

Figure 13:
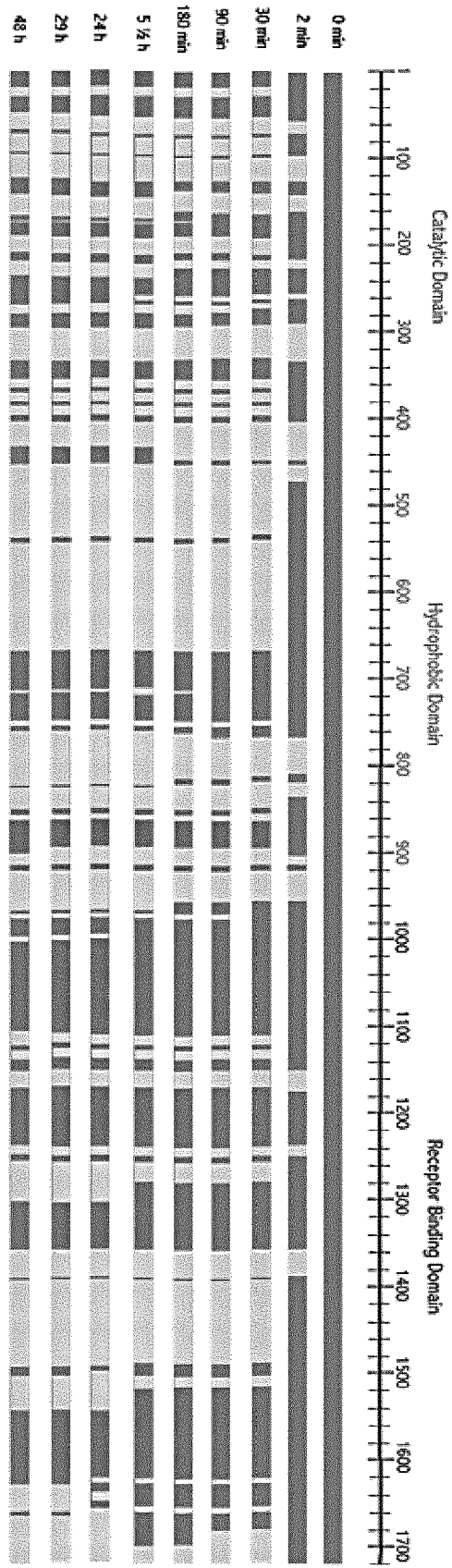

FIG. 13: MS analysis of limited proteolysis of hCyaAm in the presence of 0.5 mM calcium. Proteolysis of hCyaAm was done at a trypsin:CyaA ratio of 1:40 in the presence of 0.5 mM CaCl2 and quenched at various time points by AEBSF and frozen into liquid nitrogen.

Figure 14:
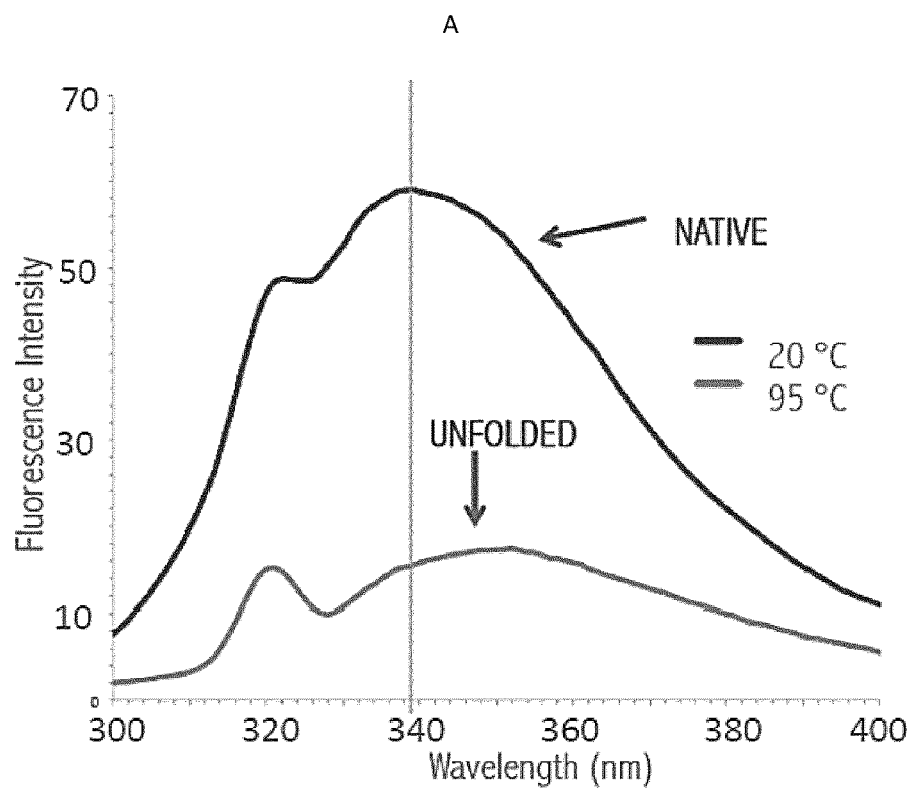
Figure 14:
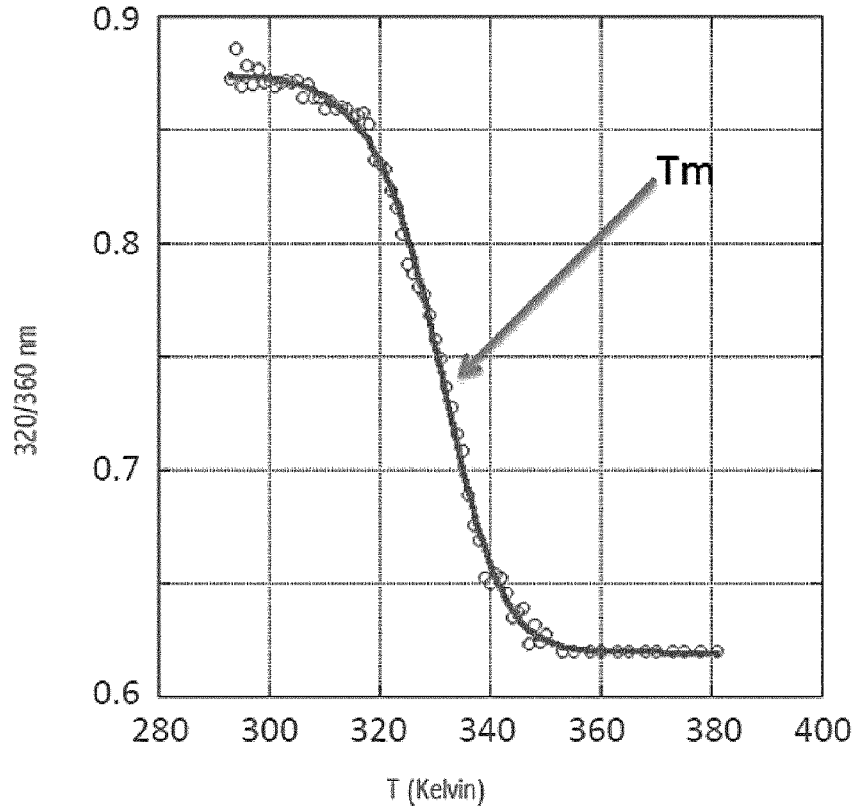

FIG. 14: Temperature unfolding of hCyaAm followed by Tryptophan fluorescence. (A) At low temperature (20° C.), the folded state of hCyaAm is accumulated while at high temperature (95° C.), the unfolded state is populated. (B) Tm is the temperature at which half of the protein is denaturated.

Figure 15:
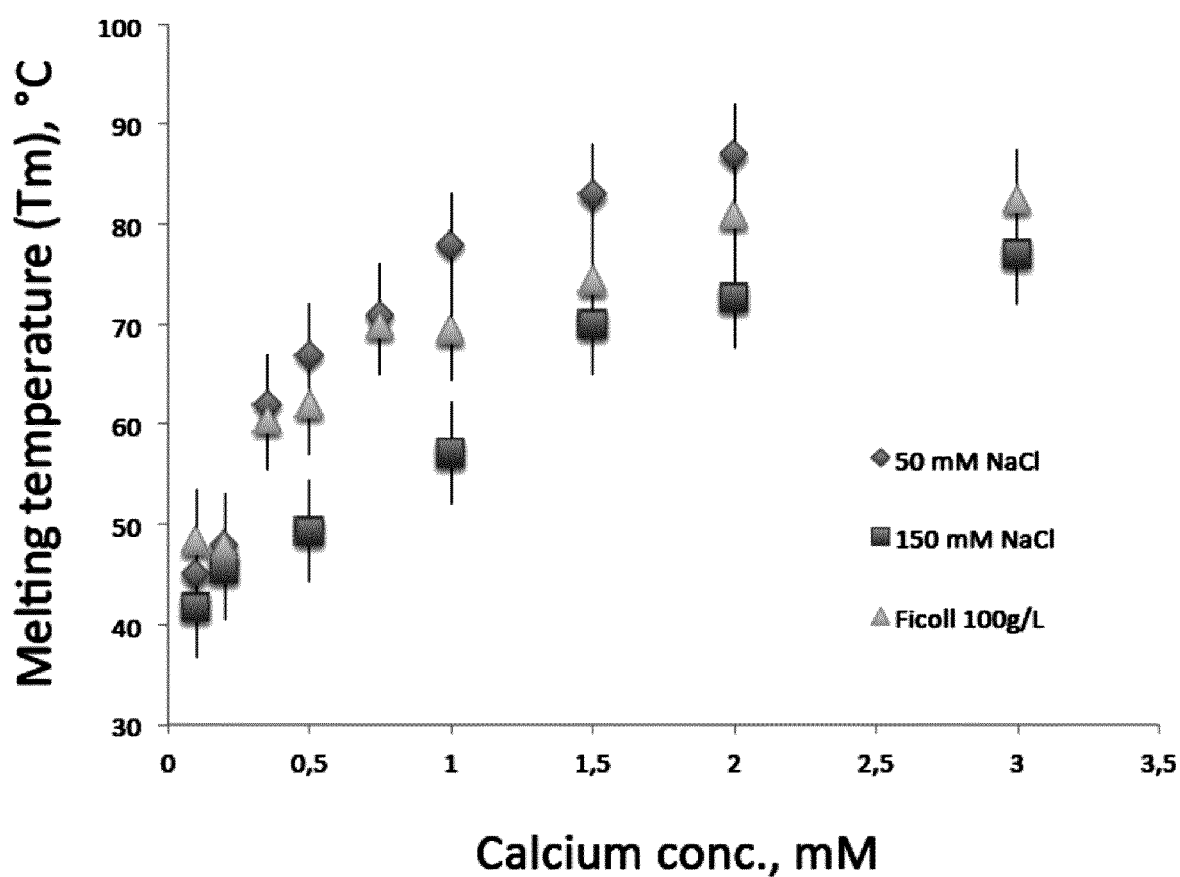

FIG. 15: Thermal stability of hCyaAm followed by Tryptophan fluorescence. Tm values of hCyaAm denatured at several concentrations of calcium, in the presence of 50 mM NaCl, 150 mM NaCl, or Ficoll70 100 g/L.

Figure 16:
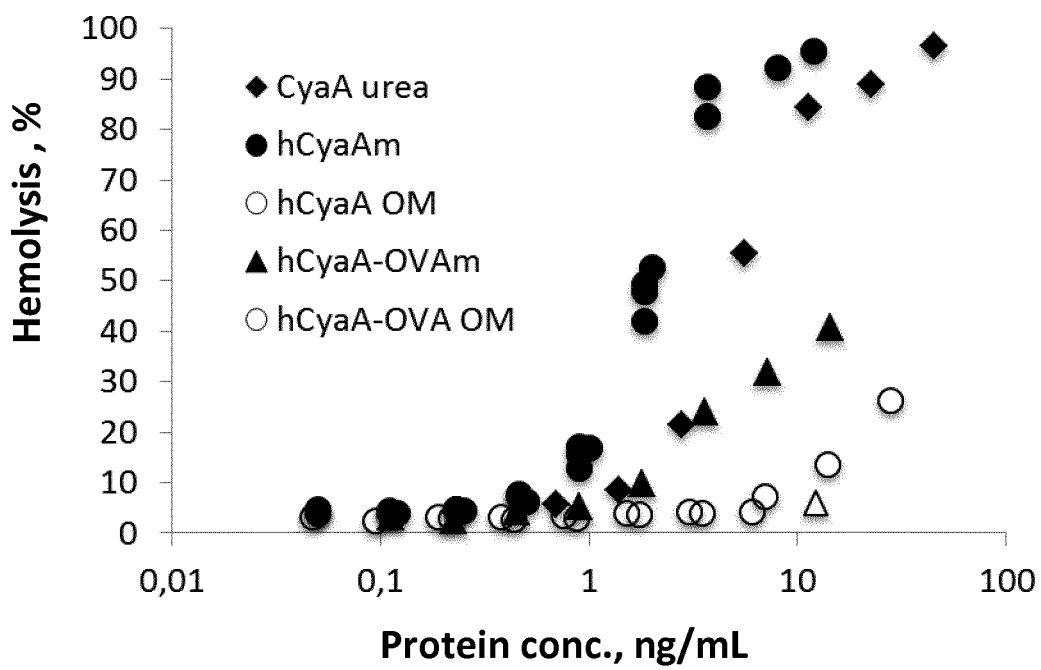
Figure 16:
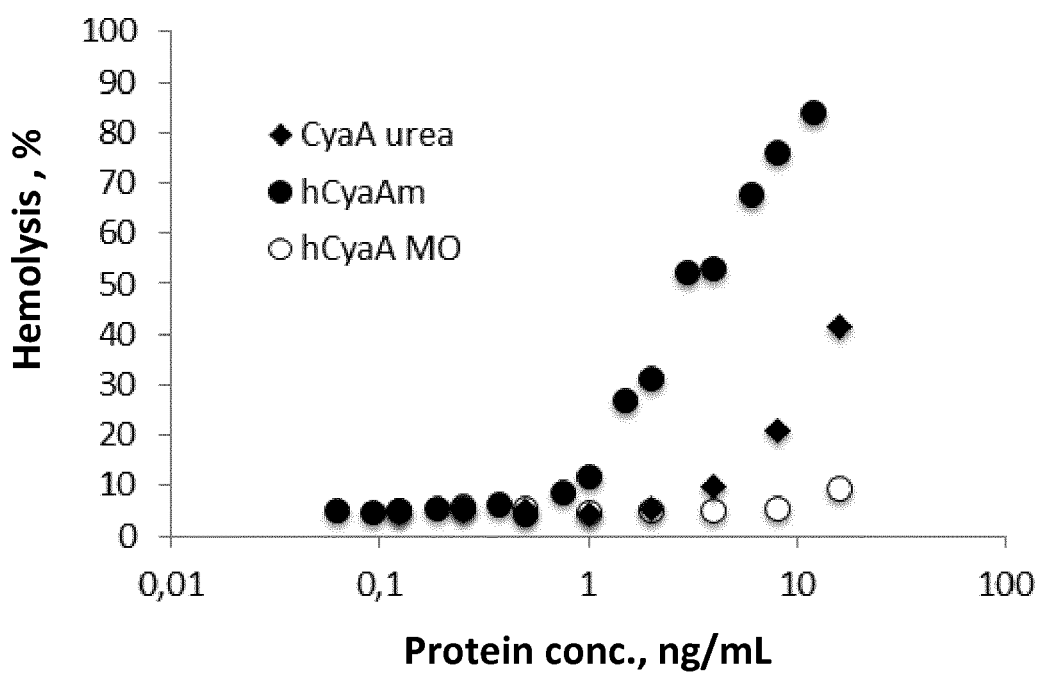
Figure 16:
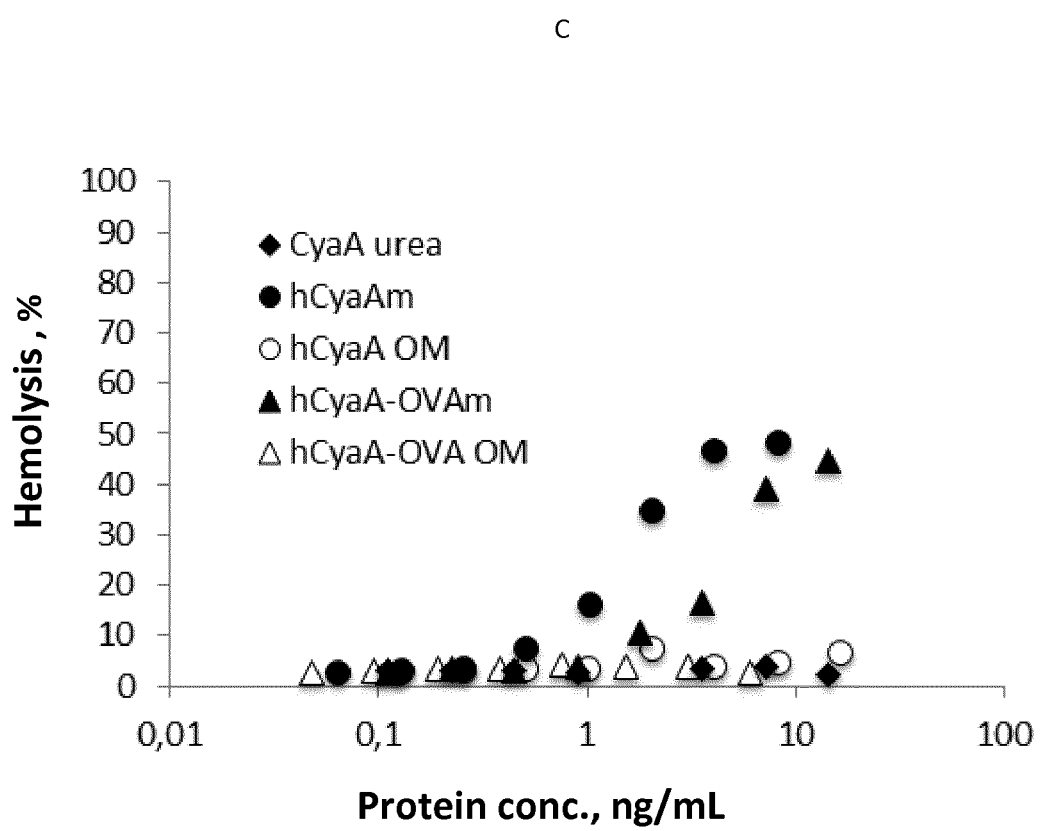

FIG. 16: Hemolysis activity of CyaA in different states. Hemolysis of red blood cells by hCyAm, CyaA urea, hCyaA OM, hCyaA-OVAm, and hCyaA-OVA OM at various concentrations of said proteins. (A) proteins and RBC in 2 mM calcium, (B) proteins and RBC in calcium-free buffer, (C) proteins in calcium-free buffer and RBC in 2 mM EDTA.

DESCRIPTION OF THE INVENTION

The present invention is related to the production and optimization of a calcium-loaded (holo-state), monomeric, stable and functional CyaA toxin, hereafter called "the CyaA toxin of the invention" (or "hCyaAm", for "holo-CyaA" monomer).

The present inventors herein show for the first time that the dilution processes used in the prior art to refold the CyaA toxin into an urea-free buffer lead to the formation of non-functional multimers. In particular, ANS (8-anilino-1-naphthalene sulfonate) fluorescence experiments showed that upon refolding, hydrophobic regions are exposed to the solvent, favoring intermolecular interactions between CyaA proteins by hydrophobic effect, thereby favoring the multimerisation of the CyaA toxin and decreasing its biological efficiency.

The present inventors observed that, surprisingly, it is possible to limit these intermolecular interactions and to drastically enhance the amount of monomeric hCyaA by refolding the CyaA toxin by using a procedure relying on the excluded volume effects induced by molecular confinement.

More precisely, the inventors showed that high amount of monomeric hCyaA can be obtained by performing size exclusion chromatography (SEC) with a matrix made of small pores. With this respect, they showed a direct relationship between pore size on SEC and the proportion of monomers: smaller the matrix pores, better the monomer yield. Moreover they identified optimized conditions to increase the proportion of monomers. As detailed in the examples below, they showed that CyaA refolding into the monomeric state is critically dependent upon the presence of calcium and protein acylation.

In particular, it is demonstrated here for the first time that CyaA acylation is critical for its folding into a monomeric and functional form. Moreover, excluded volume procedures in the presence of calcium are strictly required to refold the acylated protein into functional and stable hCyaAm.

Without being bond to the theory, it is hypothesized that calcium binding is mandatory for the formation of monomers, because it may kinetically favor native folding and bury of hydrophobic regions. On the contrary, in the absence of calcium, a slower kinetics of folding into the apo-state may favor intermolecular interactions between folding intermediates and would thus increase the population of multimer species. Furthermore, the presence of hydrophobic acyl chains on CyaA may significantly modify the local free-energy landscape of the polypeptide chain. Shielding of these acyl chains into a nascent hydrophobic core may have a major thermodynamic contribution in restricting the temporal and conformational spaces accessible to CyaA upon refolding.

In a first aspect, the present invention therefore relates to a method to produce a monomeric, stable and functional CyaA toxin, comprising the steps of:

i) Providing a sample containing denatured and acylated CyaA toxin, ii) Refolding said CyaA toxin under molecular confinement in the presence of calcium, thereby obtaining said monomeric, stable and functional CyaA toxin.

As used herein, the term "CyaA" or "CyaA toxin" designates the adenylate cyclase or adenylyl cyclase enzyme, that is able to catalyze the conversion of ATP to 3',5'-cyclic AMP (cAMP) and pyrophosphate (enzymatic activity also described as EC 4.6.1.1.). Preferably, this toxin can originate from Bordetella bacteria. These bacteria for example belong to the species Bordetella parapertussis, Bordetella hinzii, Bordetella bronchiseptica, Bordetella avium and more specifically Bordetella pertussis. In a preferred embodiment, the CyaA toxin produced in the method of the invention is the Bordetella pertussis adenylate cyclase of SEQ ID NO:1, an active fragment thereof, or a mutated form thereof. In another preferred embodiment, the CyaA toxin produced in the method of the invention is the Bordetella parapertussis adenylate cyclase disclosed under accession number CAB76450, referred to as SEQ ID NO:7 in WO 2010/136231. In another preferred embodiment, the CyaA toxin produced in the method of the invention is the Bordetella bronchiseptica adenylate cyclase disclosed under accession number CAA85481, referred to as SEQ ID NO:9 in WO 2010/136231. In another preferred embodiment, the CyaA toxin produced in the method of the invention is the Bordetella hinzii adenylate cyclase disclosed under accession number AAY57201, referred to as SEQ ID NO:8 in WO 2010/136231.

As used herein, an "active fragment of CyaA" is a fragment of CyaA which exhibits at least one function of CyaA. Preferably, said fragment contains at least one functional domain of CyaA, including the N-terminal catalytic domain of CyaA (residues 1 to 400 of SEQ ID NO:1), the translocation region of CyaA (residues 400 to 500 of SEQ ID NO:1), the hydrophobic region of CyaA (residues 500 to 750 of SEQ ID NO:1), the acylation region of CyaA (residues 800 to 1000 of SEQ ID NO:1), the RTX-containing receptor-binding domain of CyaA (RD, residues 1000 to 1706 of SEQ ID NO:1), or any combination of these domains. It may for example be the hemolytic moiety, encompassing the carboxy-terminal 1306 residues of SEQ ID NO:1 which is responsible for the pore-forming (hemolytic) activity of CyaA.

These fragments of CyaA should contain the Lys860 and Lys983 residues that are known to be acylated.

As used herein, the term "mutated form of CyaA" designates polypeptides that present at least one mutation in their amino acid sequence, as compared with the amino acid sequence of the wild-type CyaA. This mutated form may share, for example, at least 70%, preferably at least 80%, more preferably at least 90% identity with wild-type CyaA. Preferably, the identity percentage between a mutated form and the wild-type CyaA of SEQ ID NO:1 is identified by a global alignment of the sequences in their entirety, this alignment being performed by means of an algorithm that is well known by the skilled person, such as the one disclosed in Needleman and Wunsch (61). Accordingly, sequence comparisons between two amino acid sequences can be performed for example by using any software known by the skilled person, such as the "needle" software using the "Gap open" parameter of 10, the "Gap extend" parameter of 0.5 and the "Blosum 62" matrix.

This mutated form of CyaA may have the same catalytic, haemolytic, immunogenic, activities or CD11/CD18 cell-binding or translocation properties as the wild-type CyaA, or different activities or properties.

In a preferred embodiment, the monomeric CyaA refolded through the method of the invention will be used for therapeutic purposes in animals (as a vaccination or antigen-delivery means, see below). A reduced hemolytic and/or catalytic activity may thus be required, so as to decrease its cellular toxicity and improve its safety. In this particular embodiment, the mutated form of CyaA will therefore have to exhibit a reduced hemolytic and/or catalytic activity as compared to the wild-type CyaA. In a more preferred embodiment, the mutated form of CyaA will be devoid of the pore-forming activity exhibited by the wild-type CyaA. This absence of pore-forming activity of CyaA can be measured using the single whole cell patch-clamp experiment disclosed in WO 2010/136231.

Reduced hemolytic activity has been observed for *B. pertussis* or *B. parapertussis* CyaA toxins that are mutated on positions 570 and 860 (said mutations being preferably E570Q and K860R), and for *B. bronchiseptica* CyaA that is mutated on positions 569 and 859 (said mutations being preferably E569Q and K859R). Details on these mutated forms of CyaA are provided in WO 2010/136231 which is incorporated herein by reference.

Moreover, it may also be interesting to use detoxified CyaA toxin. Detoxification may be achieved by inserting amino acid residue(s) (e.g., a dipeptide) in the catalytic domain of CyaA. Efficient detoxification has been observed for example by inserting the LQ dipeptide between residues 188 and 189 of CyaA (cf. the international application WO2005/089792 which is incorporated herein by reference).

Importantly, these mutated forms of CyaA should however still be able to bind the cell surface CD11b/CD18 receptor so as to target the toxin to Antigen Presenting Cells (APCs). The capacity of a mutated CyaA to target CD11b/CD18 cells can be assayed by using any of the methods disclosed in WO 2002/22169, which is incorporated herein by reference, or in El-Azami-El-Idrissi M. et al., (60).

Finally, when used as antigen-delivery vectors, these mutated forms should be capable of efficiently translocating their N-terminal domain (or the molecule inserted in said domain, or grafted on it) into the targeted cells. This capacity can be assayed by applying the method described in WO 2002/22169.

It is also possible to use a CyaA toxin in which residues 225-234 have been deleted, as proposed in WO2005/089792 which is incorporated herein by reference.

Also, these mutated forms of CyaA should contain the Lys860 and Lys983 residues that are known to be acylated.

All these CyaA fragments or mutants can be refolded thanks to the method of the invention, thereby generating monomeric CyaA toxin that can safely be used in therapeutic applications.

In a particular embodiment, the CyaA toxin, fragment thereof or mutant thereof is used as antigen-delivery vector or protective antigen for vaccination purposes. In these cases, it may be useful to generate recombinant CyaA toxin in which (or to which) exogenous antigenic polypeptides are inserted (or chemically coupled). Thus, the CyaA toxin produced in the method of the invention, its fragment or its mutated form, may comprise an antigen/epitope that is intended to be delivered in the cytosol of the target cells. This antigen/epitope may be inserted within the CyaA polypeptide or chemically grafted thereto. As mentioned previously, the CyaA toxin is naturally produced by the *Bordetella* bacterial cells, especially *Bordetella pertussis*. Moreover, it can be produced as a recombinant protein in other bacterial cells, such as *E.coli*, provided that said bacteria co-express CyaC to permit its post-translation acylation (2,53).

In these recombinant cells, CyaA mainly accumulates in inclusion bodies, requiring denaturing conditions for its solubilization. Extraction and purification of the CyaA toxin from these inclusion bodies have been described earlier (1, 2, 41, 49, 52). These procedures may be adapted by the skilled person, for example by adding some chromatographic steps in order to obtain a protein free of lipopolysaccharide (LPS) and of other contaminants. An example thereof is provided in the Material and Methods below. These procedures are routinely used by the skilled technicians. The thus obtained CyaA toxin is then usually stored in buffers containing a denaturing chaotropic agent such as urea (typically higher than 6 M), to maintain it in a soluble form (2, 41, 49, 52).

The aim of the present invention is to refold the denatured CyaA proteins that have been purified from these inclusion bodies and consequently stored in denaturing storing buffers, so as to produce a monomeric, stable and functional form of the CyaA toxin, that does not need to be stored in denaturing conditions.

The present inventors herein show that one monomer of CyaA has a hydrodynamic radius comprised between 4.9 and 5.5 nm (as measured by dynamic light scattering or velocity AUC) and a molecular mass of about 177 kDa (as measured by SEC-TDA or equilibrium AUC). The term "monomeric CyaA" therefore characterizes non-aggregated CyaA toxins that remain monodispersed in solution, and that share the hydrodynamic radius and molecular mass determined by the present inventors. More specifically, "monomeric CyaA toxins" correspond to non-aggregated CyaA toxins having a molecular mass of about 177 kDa.

By "stable", it is herein meant that the CyaA toxin refolded with the method of the invention remains monomeric although not kept under denaturing conditions (i.e., keeps the constant size and homogenous structure disclosed above). In particular, a stable CyaA toxin remains structurally monomeric after several cycles of freezing/thawing and upon long-term storage (up to 6 months).

By "functional", it is herein meant that the CyaA toxin refolded with the method of the invention exhibits a biological activity. Said "biological activity" may correspond to the CyaA catalytic activity, the CyaA pore-forming activity (or hemolytic activity), the CyaA ability to bind to the CD11b/CD18 receptor, the CyaA ability to translocate its N-terminal part into the cytosol of targeted cells, or the CyaA ability to induce cAMP synthesis in eukaryotic target cells. Specifically, it may be related to the antigen-delivery properties of CyaA, a functional CyaA toxin being capable to bind to CD11b/CD18 expressing Antigen-Presenting Cells and deliver exogenous antigenic polypeptides inserted within CyaA or coupled to same. Said CyaA should preferably be capable to translocate its catalytic domain or the antigenic polypeptides inserted in, or chemically grafted to, in the cytosol of the target cell. It may also be related to the immunological properties of the CyaA toxin, that is, the ability of the CyaA polypeptide to induce specific immune responses (antibody- or cell-mediated) able to neutralize the toxin and/or protect a vaccinated host against infection by *Bordetella* pathogens.

Importantly, a "functional" CyaA toxin is a CyaA toxin exhibiting at least one of the above-mentioned properties (e.g., hemolytic, CD11b/CD18 binding, cytosolic translocation, or cAMP production). Some of these different functions are detailed in WO 2010/136231 and WO 2005/089792, which also disclose the technological means to measure same.

The method of the invention is necessarily performed on a sample containing denatured and acylated CyaA toxin. This sample will be hereafter referred to as "the sample of the invention" or the "CyaA sample of the invention" (as opposed to the solution containing refolded monomeric CyaA, which results from the method of the invention and which will be referred to as the "resulting CyaA solution"). The sample of the invention is obtained by purifying the inclusion bodies of bacterial cells, and contains natural or recombinant CyaA toxins in a denatured state.

Of note, "denatured" (or "unfolded") proteins are altered proteins that do not exhibit the quaternary, tertiary and secondary structures they have in their native states (but the peptide bonds of the primary structure are intact). Such alterations can be caused by external stresses and/or compounds (e.g., a strong acid or base, a concentrated inorganic acid salt, an organic solvent, radiation or heat). In a preferred embodiment, denaturation of the CyaA toxin used in the method of the invention is due to its purification and/or storage in the presence of a chaotropic agent (see below). Denaturation state of a protein can be visualized by tryptophan intrinsic fluorescence (tryptophan residues being used as macroscopic probe of protein folding), by ANS fluorescence (3) (that is sensitive to the presence of solvent-exposed apolar surfaces made of organized hydrophobic residues on the protein) or by far-UV circular dichroism (4) (ellipticity changes at 220 nm being used to follow secondary structural changes) at 25° C., as disclosed in the experimental part below.

Only "acylated" CyaA toxins can be refolded efficiently by means of the method of the invention (as shown in the experimental part below, the inactive precursor proCyaA, which is not acylated, cannot be properly refolded). An "acylated" CyaA toxin therefore designates a CyaA toxin in which the Lys860 and Lys983 residues (or corresponding Lysine residues) are acylated, as reported earlier (19).

The sample of the invention can be any buffered aqueous solution having a pH comprised between 7 and 11, preferably between 9 and 11 (typically Hepes 20 mM, pH 9-10).

In a preferred embodiment, this sample contains between 0.1M and 10M, preferably between 4M and 8M of a chaotropic agent that maintains the CyaA toxin in the denatured state described above. Of note, a minimal amount of 4M of a chaotropic agent is required, in order to avoid the aggregation of the CyaA toxin.

A chaotropic agent is a molecule in water solution that can disrupt the hydrogen bonding network between water molecules. More specifically, it increases the entropy of the system by interfering with intramolecular interactions mediated by non-covalent forces such as hydrogen bonds, van der Waals forces, and hydrophobic effects. In the context of the invention, the chaotropic agent contained in the CyaA sample of the invention is preferably chosen in the group consisting of: butanol, ethanol, guanidium chloride, lithium perchlorate, lithium acetate, magnesium chloride, phenol, propanol, sodium dodecyl sulfate (SDS), thiourea, and urea. In a preferred embodiment, this chaotropic agent is urea.

It is furthermore recommended adding a calcium salt in said sample, in order to help the refolding of the CyaA toxin under the appropriate monomeric form.

Calcium salts that may be added in said sample are preferably chosen in the group consisting of: calcium carbonate ($CaCO_3$), calcium chloride ($CaCl_2$), and calcium citrate. Calcium chloride is preferred. A final concentration of calcium salt up to 10 mM, preferably comprised between 1 and 10 mM, more preferably comprised between 2 and 4 mM, is recommended.

The present inventors have shown that the proportion of monomers versus multimers after refolding is dependent upon the initial concentration of the unfolded CyaA toxin present in the initial sample (see example 2.2. and FIG. 4C). Concentration of the CyaA toxin within the sample of the invention is therefore preferably comprised between 0.01 and 10 mg/mL. More preferably, the concentration of the CyaA toxin within the sample of the invention is comprised between 0.1 and 5 mg/mL. Even more preferably, the concentration of the CyaA toxin within the sample of the invention is comprised between 0.2 and 3 mg/mL. In other terms, the concentration of the CyaA toxin within the sample of the invention is preferably comprised between 0.05 and 50 µM, more preferably between 0.5 and 2.5 µM, even more preferably between 1 and 15 µM.

This concentration can be determined spectrophotometrically from the absorption at 280 nm using a molecular extinction coefficient of 144 000 M-1 cm-1. If need be, such a concentration can be obtained by diluting a concentrated CyaA stock solution. In this case, a dilution buffer containing between 1 and 5 mM of a calcium salt (typically 2 mM $CaCl_2$) and between 4 and 10M of a chaotropic agent (typically 6M urea) is used to achieve the desired concentration. Preferably, this dilution buffer has a basic pH (typically between 9 and 10).

Finally, the sample of the invention is preferably free of any other proteins or contaminants. More preferably, it contains more than 80%, more preferably more than 90% of the denatured CyaA toxin. This purity can be judged by SDS PAGE analysis. Even more preferably, this sample contains less than 1 EU of LPS/µg of protein. This can be assessed by a standard LAL assay.

The method of the invention therefore requires the refolding of the CyaA toxin under "molecular confinement". Molecular confinement of CyaA can be obtained by filtering the CyaA-containing sample on a matrix having small pore size, or on a matrix containing small porous beads of small pore size, or by adding soluble molecular crowding agents in same. Molecular confinement can be obtained by any other means increasing the excluded volume where the refolding process is achieved.

Crowding agents are for example inert molecules such as polyethylene glycol or ficoll (such as ficoll 70), that mimic crowding effects and increase the excluded volume when added in high concentrations in the sample containing the denatured CyaA toxin.

In a preferred embodiment, said molecular confinement is achieved by gel filtration.

In a more preferred embodiment, said molecular confinement is achieved by performing size-exclusion chromatography (SEC) on a matrix containing small porous beads. In this case, the diameter of said beads is preferably smaller than or equal to 10 µm, and it is more preferably of about 8 µm. Moreover, the pores contained in said beads have preferably a diameter smaller than 0.1 µm, more preferably comprised between 20 and 50 nm, even more preferably of about 45 nm.

Of note, and as shown in the experimental part below, the smaller the bead and pore diameters are, the higher the monomer/multimer ratio will be.

In a preferred embodiment, the inventors propose to apply molecular confinement on CyaA toxin molecules by contacting the sample of step i) on a column containing said beads.

Step ii) of the method of the invention may be achieved for example by using the Superdex 200, the Superose 6HR from GE Healthcare, the TSK from Tosoh, the Bio-Sec3 from Agilent, and the like (all these matrices are characterized by a bead size less than 10 μm, limiting the accessible bulk volume). It is however not recommended to use matrices having larger bead sizes, for instance the Sephacryl matrices from GE HC and G25SF (more or less 50-70 μm), so that, as demonstrated by the present inventors in the experimental part below, the monomer/multimer ratio of CyaA decreases.

The matrix contained in these columns may be of any type (silica, agarose, dextran . . . ), as the confinement properties appeared independent of the chemical composition of the matrix (see example 2.2 below).

The present inventors have shown that refolding of the CyaA toxin in a monomeric form only occurs in the presence of calcium. Thus, it is recommended that all the buffers used during the molecular confinement step ii) contain a substantial amount of a calcium salt.

Calcium salts that may be used in these buffers are chosen in the group consisting of: calcium carbonate ($CaCO_3$), calcium chloride ($CaCl_2$), and calcium citrate.

In a preferred embodiment, the buffers used during the molecular confinement step ii) contain a concentration comprised between 0.1 and 10 mM, more preferably comprised between 2 and 6 mM, even more preferably comprised between 3 and 5 mM of said calcium salt.

Moreover, the present inventors showed that the production of CyaA monomers is improved if the buffers used during the molecular confinement step ii) have a low ionic strength (favoring repulsive interactions). Consequently, in a preferred embodiment, these buffers applied to the column during the refolding process contain between 5 and 500 mM, preferably between 100 and 300 mM of an ionic salt. Said salt may affect the ionic strength of the sample. It can be for example NaCl or $NH_4CO_3$.

Finally, the present inventors showed that the production of CyaA monomers is improved if the buffers used during the molecular confinement step ii) have a rather basic pH. In a preferred embodiment, the pH of these equilibration buffers and the elution buffer is therefore comprised between 7 and 10, more preferably between 7 and 8.

The "buffers used during the molecular confinement step ii)" are for example the equilibrating buffer and the elution buffers that are used for performing size-exclusion chromatography.

In a particular embodiment, the production of high rate of monomeric CyaA toxin can be reproducibly achieved by:

a) Equilibrating the size-exclusion chromatography column such as disclosed above with an equilibrating buffer containing between 1 and 10 mM, preferably between 1 and 4 mM, of a calcium salt, b) Contacting the said chromatography column with the sample of the invention containing the denatured CyaA toxin, as disclosed above, c) Eluting the CyaA toxin from the chromatography column with an elution buffer containing between 1 and 10 mM, preferably between 1 and 4 mM of a calcium salt.

As detailed above, the sample to be contacted with the chromatography column contains the denatured CyaA toxin, and a significant amount of a calcium salt, and of a chaotropic agent. It has preferably a basic pH (typically 7-11).

Importantly, the equilibrating and elution buffers should not contain any of the chaotropic agents defined above.

A typical elution buffer contains, for example: 20 mM Hepes, 150 mM NaCl, 2 mM $CaCl_2$, pH 7.4.

In a preferred embodiment, the equilibration buffer and the elution buffer used during the SEC process have the same composition.

The chromatography assay will enable to produce and separate the monomeric forms of CyaA and the multimeric forms of CyaA, which will eluate separately. Two distinct solutions will be therefore recovered (one mainly containing CyaA monomers, and the other mainly containing CyaA multimers).

As mentioned above, the "resulting CyaA solution" herein corresponds to the solution obtained at the end of the refolding process, containing mainly CyaA monomers (the solution containing mainly CyaA multimers, although potentially useful, is not to be considered in the context of the present invention).

In a second aspect, the present invention relates to the resulting solution obtained by the method disclosed above, which contains high proportion of a calcium-loaded, monomeric, soluble, stable and functional CyaA toxin.

The resulting solution contains more than 50%, more preferably 75%, more preferably more than 80% and even more preferably more than 90% of CyaA monomers. In other words, more than 50%, more preferably more than 75%, more preferably more than 80% and even more preferably more than 90% of the CyaA toxin is under a monomeric form. In other terms, more than 50%, preferably more than 75%, more preferably more than 80% and even more preferably more than 90% of the CyaA molecules contained in the resulting solution is not aggregated.

On the other hand, the resulting solution contains preferably less than 50%, preferably less than 25%, more preferably less than 20% and even more preferably less than 10% of aggregated or multimeric CyaA.

Even more preferably, the resulting solution is essentially devoid of multimeric CyaA, meaning that less than 5% of the CyaA toxin present in the preparation is under a multimeric form.

Besides the presence of high amount of a monomeric CyaA toxin, this resulting CyaA solution has typically the same composition as the elution buffer does. It therefore advantageously contains between 1 and 10 mM, preferably between 1 and 4 mM, of a calcium salt, and does not contain any chaotropic agent. Furthermore, it has a pH comprised between 7 and 8, as the elution buffer does. Importantly, this resulting solution contains no chaotropic agent.

This solution can be stored during several months at $-20°$ C.

This resulting solution may be further concentrated by classical means so as to increase the concentration of monomeric CyaA and provide stock solutions. These classical means are for example lyophilisation, filtration (e.g., on Amicon® filters), IEC (Ion Exchange Chromatography), etc.

Consequently, in another aspect, the present invention relates to a solution containing a calcium-loaded, monomeric, stable and functional CyaA toxin.

It is reminded that the calcium-loaded, monomeric, stable and functional CyaA toxin obtained by the method of the invention exhibits the following characteristics:

a) its molecular mass is of about 177 kDa,
b) its hydrodynamic radius is of about 5 nm,
c) its melting temperature is of about 85° C.,
d) it optionally exhibits enhanced biological activities, (e.g., 5-20 times higher hemolytic and/or cytotoxic activities) as compared to that of multimeric CyaA.

In a further aspect, the present invention relates to an isolated monomeric CyaA toxin obtained by the method of the invention. This monomeric toxin is characterized at least by the molecular mass and the hydrodynamic radius described above.

The monomeric CyaA toxin obtained by the method of the invention can be used in two main applications: 1) as an antigen-delivery vector and 2) as a natural antigen for acellular *pertussis* vaccine against whooping cough.

In these two particular cases, the CyaA toxin is preferably a mutated form of the wild-type CyaA toxin of SEQ ID NO: 1, whose cytotoxic activity has been reduced, but whose binding and translocating activities into Antigen-Presenting Cells expressing CD11b/CD18 are maintained, as compared to wild-type CyaA (appropriate mutations in this purpose are provided e.g., in WO 2010/136231 and WO 2005/089792).

1) Use of the Monomeric CyaA Toxin Obtained by the Method of the Invention as Antigen Delivery Vectors for Therapeutic Vaccines Earlier studies have shown that the CyaA toxin is a potent non-replicating vector to deliver antigens into antigen presenting cells and can induce specific cell-mediated immune responses. In these applications, antigens of interest are genetically or chemically grafted, preferably into the catalytic domain of a detoxified toxin, to generate a recombinant CyaA that can be efficiently targeted in vivo to dendritic cells (DC), which express the CyaA receptor, CD 11b/CD 18. In these professional antigen-presenting cells, the grafted antigens are processed and presented to both MHC-class I and class II pathways to induce specific CD8$^+$ and CD4$^+$ T cell responses.

The method described here offers the opportunity to produce recombinant CyaA proteins (containing, or not, exogenous antigens) in their monomeric and functional forms in the absence of urea, thus facilitating handling, storage and manipulation of the vaccine molecules for clinical applications.

In another aspect, the present invention also relates to the monomeric CyaA toxin obtained by the method of the invention, for use as an antigen delivery vector.

In this case, antigens of interest or epitopes thereof can be genetically or chemically grafted to the catalytic domain of the CyaA toxin obtained under monomeric form by the method of the invention, which has preferably been detoxified, and these proteins can be administered to patients in need thereof in order to stimulate CD4$^+$ and CD8$^+$ T-cell based immune responses.

In specific embodiments, the heterologous antigen or epitope thereof is selected from the group consisting of an antigen of a bacterial pathogen, a tumoral cell antigen, a viral antigen, a retroviral antigen, a fungus antigen or a parasite cell antigen.

In this context, antigens of interest are for example immunogenic epitopes of tumor-associated antigens or of oncogenic proteins (such as the tyrosinase protein, or the E6 or E7 protein of HPV16 or HPV 18).

The present application furthermore discloses methods to stimulate CD4$^+$ and CD8$^+$ T-cell based immune responses in a patient in need thereof, comprising the step of administering to said patient a fusion protein containing a) an antigen or an epitope thereof of interest and b) the monomeric CyaA toxin obtained by the method of the invention, which has preferably been detoxified. As mentioned previously, this antigen/epitope can be genetically inserted within the monomeric CyaA toxin, or chemically coupled thereto.

In another aspect, the present invention relates to a fusion protein containing a) an antigen of interest or an epitope thereof and b) the monomeric CyaA toxin obtained by the method of the invention, which has preferably been detoxified. As mentioned previously, this antigen/epitope can be genetically inserted within the monomeric CyaA toxin, or chemically coupled thereto.

In specific embodiments, the heterologous antigen or epitope thereof is selected from the group consisting of an antigen of a bacterial pathogen, a tumoral cell antigen, a viral antigen, a retroviral antigen, a fungus antigen or a parasite cell antigen.

Preferably, said antigen of interest is an immunogenic epitope of a tumor-associated antigen or of an oncogenic protein (such as the tyrosinase protein, or the E6 or E7 protein of HPV 16 or HPV 18).

In another aspect, the present invention relates to a pharmaceutical composition containing a) the fusion protein described above and b) a pharmaceutically acceptable carrier, as described below.

2) Use of the Monomeric CyaA Toxin Obtained by the Method of the Invention as a Protective Antigen for Whooping Cough Vaccination Older versions of vaccine against *Bordetella*, especially *Bordetella pertussis*, the causative agent of whooping cough, were made of inactivated cells, i.e., chemically killed whole cell suspensions, which were subsequently discontinued due to local and systemic side reactions caused by the vaccine components. Newer versions are termed acellular vaccines, because they are made of inactivated macromolecules (combinations of PTX, FHA, pertactin and fimbriae) from *Bordetella*, especially *B. pertussis*. These acellular vaccines are more effective, have fewer side effects, are less likely to provoke a febrile state and moderate doses are required compared to whole cell vaccines. Acellular vaccine containing at least three protective antigens was shown to be of higher or similar efficacy to the previously used whole cell *pertussis* vaccine.

The adenylate cyclase produced by *Bordetella*, especially *Bordetella pertussis*, is one of the major virulence factors of this organism. CyaA plays an important role in the early stages of respiratory tract colonization by *Bordetella*, especially *B. pertussis*. Being involved in the early stages of the disease, it might be interesting to add CyaA as antigen in acellular vaccines to enforce the stimulation of the immune system at the early stage of infection. Guiso et al (62), showed that CyaA is an immunoprotective antigen. Preparation of an acellular vaccine containing CyaA produced by the prior art processes would require the presence of urea that might destabilize the other antigens (PTX, FHA, pertactin, fimbriae). Noteworthy, the use of the monomeric CyaA obtained by the method of the invention overcomes this problem because this form does not require urea to preserve its solubility.

In another aspect, the present invention also relates to the monomeric, stable and functional CyaA toxin obtained by the method of the invention, for use as a protective antigen in a whooping cough therapeutic vaccine.

In another aspect, the present invention therefore relates to a pharmaceutical composition containing a) the monomeric, stable and functional CyaA toxin obtained by the method of the invention and b) a pharmaceutically acceptable carrier.

As mentioned above, this monomeric CyaA toxin may comprise an exogenous antigen/epitope that is intended to be delivered in the cytosol of the target cells.

As used herein, a "pharmaceutically acceptable carrier" means a compound, or a combination of compounds, contained in a pharmaceutical composition, that does not cause secondary reactions and that, for example, facilitates administration of the active compounds, increases its lifespan and/or effectiveness in the organism, increases its solubility in solution or improves its storage. Such pharmaceutical carriers are well-known and will be adapted by a person skilled in the art according to the nature and the administration route of the active compounds selected. A typical pharmaceutical composition for intravenous infusion could be made up to contain 250 ml of sterile Ringer's solution. Actual methods for preparing parenterally administrable compounds will be known or apparent to those skilled in the art and are described in more detail in for example, Remington's Pharmaceutical Science, 17th ed., Mack Publishing Company, Easton, Pa. (1985), and the 18th and 19th editions thereof.

Preferably, this pharmaceutical composition contains a calcium-loaded, monomeric, stable and functional CyaA toxin obtained by the method of the invention.

More than 50%, preferably more than 75%, more preferably more than 80% and even more preferably more than 90% of the CyaA toxin present in this pharmaceutical composition is under a monomeric form.

More preferably, this pharmaceutical composition is essentially devoid of multimeric CyaA, meaning that less than 5% of the CyaA toxin present in the solution is under a multimeric form.

As explained above, this pharmaceutical composition is advantageously a therapeutic vaccine. This vaccine is preferably used to prevent whooping cough infection. Such a vaccine may also contain other antigens that could serve as immunoprotective antigen against whooping cough infection (such as PTX, FHA, pertactin, fimbriae, etc.).

These pharmaceutical compositions are aimed to be administered for example to subjects that are likely to be infected by *Bordetella* sp. bacteria especially, *B. pertussis* bacteria. More generally, these pharmaceutical compositions are aimed to be administered to patients in order to stimulate CD4$^+$ and CD8$^+$ T-cell based immune responses.

Alternatively, the pharmaceutical composition can contain the fusion protein described above as antigen delivery vector.

In other terms, the present application furthermore discloses methods to stimulate CD4$^+$ and CD8$^+$ T-cell based immune responses to patients in need thereof, comprising the step of administering to said subjects the pharmaceutical composition of the invention, as disclosed above.

As used herein, the term "subject" designates any animal and more precisely a human.

Preferably, the pharmaceutical composition of the invention will be administered by systemic route, notably by intravenous, intramuscular, intradermal, intraperitoneal, subcutaneous or oral route. More preferably, it will be administered in several doses that are spaced equally over time. Their administration routes, dosing schedules and optimal galenic forms can be determined according to the criteria generally taken into account when establishing a treatment suited to a patient.

The present application furthermore discloses methods to prevent whooping cough (especially *B. pertussis*) infection in subjects, comprising the step of administering to said subjects the pharmaceutical composition of the invention, as disclosed above.

In the light of the structural role of both calcium and acyl chains in CyaA folding demonstrated here, it appears that the procedure of the invention is applicable to other RTX cytolysins that are activated by selective acylation by dedicated CyaC-like acyltransferases and dependent upon calcium for their cytolytic activity, such as HlyA, LktA, and the like (63).

Thus, the refolding method disclosed above may be useful to obtain monomeric forms of other RTX-containing proteins, such as HlyA from uropathogenic *Escherichia coli*, LktA from *Mannheimia haemolytica*, LtxA from *Aggregatibacter actinomycetemcomitans*, ApxIA-ApxIVA from *Actinobacillus pleuropneumoniae*, ApxI-ApxII from *Actinobacillus suis*, PaxA from *Pasteurella aerogenes*, PvxA from *Proteus vulgaris*, EhxA from enterohemorrhagic *Escherichia coli*, or other members of the RTX toxins family (63).

EXAMPLES

1. Methods

CyaA Production and Purification

CyaA was produced and purified from inclusion bodies as previously described (1,2). Briefly, the inclusion bodies were solubilized in about 50 ml of 20 mM Hepes, 8 M urea, pH 7.4, by overnight solubilization under constant stirring with a magnet at 4° C. After centrifugation at 12000 rpm for 20 min, the supernatant was supplemented with 0.14 M NaCl and incubated for 1 hour at room temperature with 75 ml of Q-Sepharose resin equilibrated with 20 mM Hepes, 140 mM NaCl, 8 M urea, pH 7.4. The resin, retaining the CyaA protein, was then loaded onto a column and contaminants were washed out. After an extensive wash with the same buffer, the CyaA protein was eluted in 20 mM Hepes, 500 mM NaCl, 8 M urea, pH 7.4. The eluate was then diluted in 20 mM Hepes, 8M urea to decrease salt down to 140 mM NaCl and loaded onto a second Q-sepharose column (50 ml). Washing and elution were performed in the same conditions as described above with the first Q media. This last step further removed contaminants and concentrated the CyaA protein. Proteins eluted from the second Q-sepharose column were diluted five times with 20 mM Hepes, 1 M NaCl, pH 7.4, and applied onto a 70-ml phenyl-sepharose column equilibrated with the same buffer. Resin was washed with 20 mM Hepes, 1 M NaCl, with Hepes 20 mM and then with 50% isopropanol. The isopropanol washing step allowed the removal of many contaminants and LPS. After an extensive wash with 20 mM Hepes, the toxin was eluted with Hepes 20 mM, urea 8 M. The eluate was finally loaded onto a sephacryl 500 (GE Healthcare, HIPREP 26/60) equilibrated in 20 mM Hepes, 150 mM NaCl, 8 M urea. CyaA was then concentrated by ultrafiltration to 1-2 mg/ml and stored at −20° C. in 20 mM Hepes, 8 M urea (plus or minus 150 mM NaCl). All toxins purified by this method were more than 90% pure as judged by SDS gel analysis and contained less than 1 EU of LPS/µg of protein as determined by a standard LAL assay (Lonza). CyaA toxin concentrations were determined spectrophotometrically from the absorption at 280 nm using a molecular extinction coefficient of 144 000 M-1 cm-1. Altogether, the overall recovery from a 1.6-liter fermentor varies from 20 to 40 mg of pure CyaA proteins.

Refolding of Urea-Denatured CyaA

The renaturation of CyaA from its denatured state in 8 M urea, was followed by tryptophan intrinsic fluorescence, ANS fluorescence and circular dichroism in the far-UV ranges at 25° C. Tryptophan intrinsic fluorescence was used to follow the changes of tryptophan environment, ANS fluorescence was used to follow the changes of hydrophobic environment (3) while ellipticity changes at 220 nm was used to follow secondary structural changes (4).

Fluorescence Spectroscopy

Measurements were performed with an FP-6200 spectrofluorimeter (Jasco, Japan) in a Peltier-thermostated cell holder, using a Quartz SUPRASIL 105.251-QS (Hellma) as described elsewhere (5). A bandwidth of 5 nm was used for the excitation and emission beams. For tryptophan intrinsic fluorescence, the excitation wavelength was fixed at 290 nm. The emission spectra were recorded at 25° C., from 300 to 400 nm at a scan rate of 125 nm.min-1. For ANS fluorescence (5 µM ANS; 0.5 µM CyaA), the excitation wavelength was fixed at 360 nm. The emission spectra were recorded from 450 to 550 nm.

The renaturation of CyaA was initiated by directly diluting the CyaA protein (10 µM stored in 8 M urea, 20 mM Hepes, pH 7.4) to a final concentration of 0.5 µM into either buffer A (20 mM Hepes, 150 mM NaCl, pH 7.4) or buffer B (buffer A plus 2 mM CaCl2) supplemented with the appropriate quantity of the chaotropic agent to obtain the final urea concentration. Samples were equilibrated for 2 hours at 25° C. before fluorescence measurements. The buffer A (or buffer B) supplemented with the targeted urea concentration was used as blank and its spectrum was subtracted to each protein fluorescence spectrum. The maximum emission wavelength (λmax) values represent the average of three values obtained from emission spectra that were corrected for blank measurements.

Synchrotron Radiation Circular Dichroism Spectroscopy

Synchrotron Radiation Circular dichroism (SR-CD) spectra were recorded on DISCO beamline at the synchrotron facility SOLEIL, (Gif-sur-Yvette, France). The SR-CD experiments were carried out at 25° C., integration time of 1200 msec and a bandwidth of 1 nm with a 1 nm resolution-step. Each far-UV spectrum represents the average of 3 scans of CyaA at 5 µM. Optical cell with a 26 µm path-length and CaF2 windows (Hellma) were used for recording CD signals in far-UV region (from 180 to 260 nm). The CD units used were the mean residue ellipticity (MRE), expressed in kilodegrees square centimeter per decimole and per amino-acids ((Kdeg*cm2)/(dmol*aa)) and calculated as previously described (6).

Circular Dichroism Spectroscopy

CD spectra were recorded on an Aviv circular dichroism spectrometer model 215, equipped with a water-cooled Peltier unit as described elsewhere (7). CD measurements were carried out at a scan rate of 0.5 nm/sec (step: 0.5 nm and integration time: 1 sec) with a time constant of 100 msec and a bandwidth of 1 nm. Each far-UV spectrum represents the average of at least 5 scans. Far-UV CD spectra were recorded in rectangular quartz Suprasil cells of 0.1 mm path lengths (106.QS, Hellma). To follow the renaturation of CyaA, the stock solution (10 µM in 8 M urea, 20 mM Hepes, pH 7.4) was directly diluted to a final concentration of 1 µM either in buffer A or in buffer B adjusted with the appropriate concentration of urea. CD spectra were recorded after 1 hour of equilibration at 25° C. The buffer A or buffer B supplemented with the final urea concentrations were used as blank and their spectra were subtracted to each protein CD spectrum.

Analytical Ultracentrifugation

Sedimentation velocity experiments were performed on a Beckman XL-A analytical ultracentrifuge (Beckman Coulter) in an AN60-Ti rotor at 25° C. The samples were filtrated on 0.2 µm filters before experiments. Detection of the protein concentration as a function of radial position and time was performed by optical density measurements at a wavelength of 280 nm. The buffer was buffer A or buffer B. The computed viscosity and density of this buffer were (SEDNTERP 1.09) 0.908 cP and 1.004 g.mL-1 at 25° C., respectively. The CyaA stock solution (10 µM in 8 M urea, 20 mM Hepes, pH 7.4) was loaded onto a G25 column equilibrated in buffer A to remove urea and the collected CyaA samples (diluted to 400 µL at 1.4 µM) were supplemented or not with 2 mM CaCl2, loaded in a 1.2 mm-thick two channels epoxy centerpiece and spun at 20,000 rpm. Data were analyzed with the Sedfit software using a continuous size distribution c(s) model (7). We used the Svedberg equation to estimate the molecular mass of the species identified by sedimentation velocity assuming a frictional ratio ranging from 1.2 to 3 as acceptable values.

Size Exclusion Chromatography Coupled On-Line to a Tetra Detector Array.

Size exclusion chromatography (SEC) was carried out on TSK 4000SWxl (TOSOH, rigid spherical silica; particle size: 8 µm), Superdex200 (GE Healthcare Life Sciences, cross-linked agarose and dextran; particle size: 9-13 µm), Superose 6HR (GE Healthcare Life Sciences, agarose; particle size: 11-15 µm) and sephacryl S200 (GE Healthcare Life Sciences, copolymer of allyl dextran and N,N-methylenebisacrylamide; particle size: 25-75 µm) media. SEC was controlled by a GPCmax module connected on-line to a tetra detector array (TDA) model 302 (Malvern Instruments Ltd). The oven of the TDA contained (i) a static light scattering cell with two photodiode detectors, at 7° for low angle (LALS) and at 90° for right angle laser light scattering (RALS), (ii) a deflection refractometer, (iii) a photometer and (iv) a differential viscometer. Protein concentration was determined using both the photometer and the deflection refractometer. The RALS data coupled to the concentration provided the molecular mass. The SEC is also coupled on-line to a QELS detector (gV, Malvern Instruments Ltd), which provided the hydrodynamic radius. CyaA samples in 8 M urea or after dialysis, dilution or desalting were analyzed by SEC-TDA, following the procedures described elsewhere (8-10). Briefly, all solutions were filtered on 0.2 µm filters and allowed to equilibrate at 20° C. before SEC experiments and sample analyses were performed at 25° C. in the oven of the TDA. All experimental sequences comprised calibration injections of BSA and PEO used for TDA calibration (200 µL at 2 mg/mL). All data were acquired and processed using the Omnisec software (Malvern Instruments Ltd).

The protein batches were prepared as followed. The dialyzed CyaA in buffer A or B was obtained by incubating an aliquot of CyaA in 8M urea, 20 mM Hepes, pH 7.4 in Float-A-Lyzer G2. The desalted CyaA in buffer A or B was prepared using a 5 mL bed volume G25SF column.

Hemolysis and Intoxication Assays

The hemolytic and cytotoxic (i.e. ability to raise cAMP inside target cells) activities of the toxin were determined on sheep erythrocytes as described previously (11). Sheep erythrocytes were washed several times with buffer B and resuspended in this buffer at 5×108 cells/ml. The different CyaA samples (i.e., CyaA renatured by G25 buffer exchange, oligomeric and monomeric CyaA species collected after refolding on TSK column) were directly diluted into the erythrocytes suspension to reach the final concentration (ranging from 0.03 to 30 µg/ml for hemolytic activity and from 1 to 1000 ng/ml for the invasive activity). Control experiments were performed in the presence of excess EDTA (4 mM). The hemolytic activity was measured after an overnight incubation at 37° C. by quantifying the amount of hemoglobin released at 540 nm (and/or of intracellular content release at 405 nm). Complete lysis was obtained by addition of 0.1% Triton X100. The invasive activity was determined by measuring the intracellular cAMP accumulation. The erythrocytes suspensions were incubated with CyaA at 37° C. for 20 min, then cells were chilled on ice, centrifuged at 4° C. at 2 500 rpm for 5 min, and resuspended in buffer A supplemented with 4 mM EDTA. The cells were centrifuged similarly and the pellets were resuspended in 200 µl of buffer A plus 4 mM EDTA. After transfer into clean tubes, the samples were lysed with 400 µl of 0.1 N HCl, and boiled for 5 min at 100° C. (to inactivate any remaining adenylate cyclase). The solutions were then neutralized by addition of 400 µl of 0.1 N NaOH, and the insoluble material was removed by centrifugation at 14 000 rpm for 10 min. The intracellular cAMP content was determined by a competitive immunoassay using the "HitHunter® cAMP XS+ assay" kit (DISCOVERX) following the manufacturer instructions.

Limited Proteolysis. Full length wt CyaA monomers in buffer A in the presence of either 2 or 0.5 mM $CaCl_2$ at a final protein concentration of 0.8 uM were incubated at 20° C. with trypsin at a final concentration of 20 nM. After 30, 90, 180, 420 min, 24 & 30 h (2 mM $CaCl_2$) and 2, 5, 10, 20, 30, 90, 180, 330 minutes, 24, 29 & 48 h (0.5 mM $CaCl_2$) of trypsin treatment, the proteolysis reaction was stopped by adding AEBSF (4-(2-Aminoethyl) benzenesulfonyl fluoride hydrochloride)-trypsin inhibitor at a final concentration of 200 µM. The reaction was further quenched by immerging the sample tube in liquid nitrogen. Samples were stored at −20° C. prior mass spectrometry analysis.

Mass Spectrometry Analysis

Automated in-gel protein digestion. Stained protein spots were excised from 2D gels, and in-gel tryptic digestion was performed. Briefly, after several washing steps of gel slices, proteins were reduced and alkylated. Enzymatic digestion was performed overnight with trypsin (Trypsin Sequencing Grade, Promega, Madison, Wis., USA). A cleaning step using C18 Ziptip® was used for all samples and eluted in 10 µl (AcN/H2O/HCOOH) (75/5/0.1) (v/v/v). Peptides were dried down and resuspended in 20 µL solvent A ($H_2O$: Acetonitrile: FA; 98:2:0.1) prior to mass spectrometry (MS) analysis. The same protocol—was applied for the liquid digestions.

Mass spectrometry analysis, database search, and protein identification. Digests were analyzed on an LTQ-Orbitrap Velos instrument (Thermo Fisher Scientific, Bremen) equipped with a nano-HPLC Ultimate 3000 system (Dionex, Amsterdam, The Netherlands). Five microliters of each sample were loaded on a $C_{18}$ trap column (300 µm inner diameter×5 mm; Dionex) and peptides were further separated on an in-house packed 15 cm nano-HPLC column (75 µm inner diameter) with $C_{18}$ resin (3 µm particles, 100 Å pore size, Reprosil-Pur Basic $C_{18}$-HD resin, Dr. Maisch GmbH, Ammerbuch-Entringen, Germany). Sample loading was performed with a flow rate of 30 nL/min during 5 min then a flow rate of 300 nL/min was used for peptide separation on the analytical column. A 40 min gradient was used with the following conditions: 5 min 4% solvent B ($H_2O$: Acetonitrile: FA; 20:80:0.08), 4-40% solvent B within 15 min, 40-95% solvent B within 0.1 min, 95% solvent B for 5 min, 15 min 4% solvent B. The instrument method for the LTQ-Orbitrap Velos was set up in data dependent acquisition mode. After a survey scan in the Orbitrap (resolution 60,000), the 15 most intense precursor ions were selected for CID fragmentation in the ion trap. The normalized collision energy was set up to 35 eV during 10 ms. Minimum signal threshold for triggering an MS/MS event was set to 5,000 counts. For internal mass calibration the 455,120025 ion was used as lock mass. Charge state screening was enabled, and precursors with unknown charge state or a charge state of 1 were excluded. Dynamic exclusion was enabled for 90 s.

Raw files were processed with Mascot v.2.4.1 as search engine on Proteome Discoverer version 1.4.0.288 (Thermo Fisher Scientific, Bremen) against Swissprot database. Trypsin was chosen as specific enzyme with a maximum number of 2 missed cleavages. Possible modifications included carbamidomethylation (Cys, fixed) and oxidation (Met, variable). Mass tolerance for MS was set to 10 ppm and 0.5 Da was used for MS/MS. Probability assignment and validation was performed using Scaffold software (version Scaffold 3.5.1, Proteome Software Inc., Portland, Oreg.). A false-discovery rate of 1% was used for both peptide and protein identification.

Thermal stability of hCyaAm. Denaturation of full length wt CyaA monomers in the presence of various concentrations of $CaCl_2$ followed by Intrinsic fluorescence of Trp: Full length wt CyaA monomers were diluted in Hepes 20 mM, NaCl 150 mM, pH 7.4 (buffer A) to reach a final concentration of 50 nM in the presence of different concentrations of $CaCl_2$ (0, 0.2, 0.5, 1, 2, 3, 4 & 6 mM). Temperature interval scanning from 20 to 98° C. with a temperature gradient step of 1° C. was used. The excitation wavelength was set at 290 nm, emission and excitation slits at 5 nm. Fluorescence emission spectra were recorded from 300 to 400 nm on a JASCO FP 8200 spectrofluorimeter (Jasco, Tokyo, Japan) by using a 1 cm pathlength quartz cell (111-QS, 10×10 mm, Hellma Analytics). Curves were fitted using Kaleidagraph, Version 4.1.3, Synergy Software.

Time-Stability of hCyaAm. Time stability experiments were carried out by monitoring the elution profiles of proteins in various calcium concentrations over time using Size Exclusion Chromatography. Briefly, CyaA monomers at a final concentration of 1 µm in Hepes 20 mM, NaCl 150 mM in the presence of various concentrations of calcium (0, 0.1, 0.2, 0.5 and 2 mM $CaCl_2$) were loaded into a loop of an Akta Pure Chromatography System (GE Healtcare). At selected time points, fractions of sample were injected into a Superdex™ 200 10/300 GL to evaluate the proportions of monomers, oligomers and multimers.

Hemolysis. Erythrocytes were tested for hemolysis with various preparations of CyaA and CyaA-OVA. Red blood cells were prepared as described in Karst et al., 2014. After the last wash of RBC, cells were incubated in buffer A in the presence of 2 mM Caclium, or 2 mM EDTA or buffer A alone. The monomeric species of CyaA and CyaA-OVA (hCyaAm and hCyaA-OVAm), were used as such, or desalted on G25 equilibrated in buffer A alone, or complemented with 2 mM EDTA before dilution into cells. CyaA in 6M urea was desalted onto G25 equilibrated with buffer A+2 mM calcium. For the experiments in the absence of free calcium in samples, this batch of CyaA was further re-desalted in buffer A to remove any free calcium in the solution. The remaining calcium corresponds to calcium ions bound to CyaA.

2. Results 2.1. Folding of CyaA by Dilution, Dialysis or Desalting

The folding process of the CyaA toxin was characterized starting from the unfolded state in 8 M urea at neutral pH. The recombinant CyaA toxin used hereafter was purified essentially as previously described (ref and materiel and methods), apart that an additional step of size-exclusion chromatography (SEC) in the presence of 8 M urea was added to improve the protein purity (see material and methods). The CyaA toxin was stored at −20° C. in 20 mM Hepes, 150 mM NaCl, 8 M urea, pH 7-8. The Inventors first investigated the refolding process of CyaA as a function of urea concentration in the absence (apo-state) and in the presence (holo-state) of calcium by intrinsic fluorescence of tryptophan, by ANS fluorescence and by far-UV circular dichroism (FIG. 1). CyaA contains 15 tryptophan residues that can be used as a macroscopic probe of protein folding, while ANS fluorescence is sensitive to the presence of solvent-exposed apolar surfaces made of organized hydrophobic residues on the protein. The folding process was studied in 20 mM Hepes, 150 mM NaCl, pH 7.4 in the absence (buffer A) or in the presence of 2 mM CaCl2 (buffer B).

Both tryptophan and ANS fluorescence data showed that CyaA was unfolded in the presence of urea at concentrations higher than 4 M (FIGS. 1A and 1B) with an intrinsic fluorescence maximum emission wavelength at 355 nm typical of tryptophan side-chains fully exposed to the solvent and a maximum emission wavelength of ANS at 520 nm indicating the absence of solvent-exposed hydrophobic surface. Below 4 M urea, both tryptophan and ANS maximum emission wavelength of fluorescence changed, indicating that tryptophan residues were less exposed to the solvent, reaching a more apolar environment (FIG. 1A) and that solvent-exposed hydrophobic patches were formed (FIG. 1B). The main refolding steps of CyaA in the presence of calcium were initiated at 4 M and essentially completed at 2 M urea while in the absence of calcium the refolding appeared less cooperative, occurring between 4 and 0 M urea.

The refolding of CyaA was then explored by circular dichroism in the far-UV region. The CD spectra of CyaA in 6 M urea both with and without calcium were typical of unfolded proteins (FIG. 1C). The far-UV CD spectra of CyaA after extensive dialysis against buffer in the absence or in the presence of 2 mM calcium, showed that CyaA had acquired significant secondary structure elements. The split π-π band and the higher intensity of the n-π band around 220 nm of the CD spectrum of the protein batch in the presence of calcium suggest a higher content of helical structure as compared to the CyaA sample in the absence of calcium. The secondary structure content of CyaA upon refolding by dilution of urea was then followed at 220 nm as a function of urea concentrations (FIG. 1D). The secondary structure changes as a function of urea concentrations were similar to the tryptophan or ANS fluorescence changes, suggesting that the folding of secondary and tertiary structures occurred in a concerted manner.

The various CyaA batches were then analyzed by size exclusion chromatography (SEC) followed by a tetra detector array (TDA). The right angle static laser light scattering (RALS) combined with the UV detector signals allows molecular mass determination while the quasi-elastic light scattering (QELS) provides the hydrodynamic radius (RH) of the eluting species. CyaA (in 8 M urea) when loaded on a TSK column equilibrated in 20 mM Hepes, 150 mM NaCl, pH 7.4 (buffer A) containing 4 M urea, eluted as a broad peak with a molecular mass of 180±10 kDa (FIG. 2A) and an averaged RH of 12±2 nm (FIG. 2B), indicating that CyaA in these conditions was monomeric and unfolded. CyaA was then dialyzed against buffer A or B (i.e., in the absence or in the presence of 2 mM calcium) and analyzed similarly by SEC-TDA. The CyaA dialyzed without calcium eluted mainly as multimeric species with molecular masses ranging between 500 and 2000 kDa (FIG. 2C). A similar profile was observed with the CyaA dialyzed in the presence of calcium, albeit a weak peak around 14 mL likely corresponding to a monomeric form could be detected (FIG. 2D).

In an other set of experiments, the urea was removed from the CyaA samples by using a rapid buffer exchange by chromatography on a Sephadex G-25 Superfine desalting column instead of the dialysis procedure. The desalted CyaA samples were then analyzed similarly by SEC-TDA on the TSK column. As shown in FIG. 2 (E & F), CyaA refolded by buffer exchange in the absence of calcium eluted mainly as multimers while a significant quantity of monomeric forms could be detected in the sample desalted in the presence of calcium. Collectively, these data indicate that although the urea-unfolded state is monomeric, upon removal of urea by dialysis or by a desalting procedure, CyaA formed mainly multimeric species both in calcium-free or in calcium-containing buffers, in agreement with prior studies (41,49).

Analytical ultracentrifugation (AUC) was performed to further analyze the CyaA samples obtained by refolding through the gel filtration buffer exchange procedure (FIGS. 2E and 2F). AUC was done either in the absence (FIGS. 3A and 3B) or in the presence of 2 mM calcium (FIGS. 3C and 3D). The distribution of sedimentation coefficients (FIG. 3E) shows that in the absence of calcium, the main population is centered on 12 S corresponding to multimers, mainly dimers to tetramers while a weak population around 6 S, may correspond to a monomeric species in the apo-state. In the presence of calcium, a broad distribution of multimers was observed from 10 to 45 S with a minor peak at 7-8 S likely corresponding to the monomeric population of holo-CyaA.

2.2. Molecular Confinement is Required to Produce Monomeric CyaA.

The results described above showed that CyaA folding is initiated below 4 M urea with a concomitant formation of secondary and tertiary structures, and appearance of solvent-exposed hydrophobic surfaces that are probably involved in the aggregation process leading to the multimeric states of CyaA. It was hypothesized that molecular confinement of CyaA during the refolding process could decrease the intermolecular interactions between the polypeptides and could thus reduce potential aggregation. An experimental approach to confine proteins is to use gel filtration on matrix characterized by small particle and pore sizes. To test this hypothesis, the unfolded CyaA (in 8 M urea) was directly loaded onto a TSK 4000SWxl column made of a matrix of particle size of 8 μm and pore size dimension of ≈45 nm (see material and methods section) and equilibrated in buffer B. FIG. 4A shows the UV and molecular mass profiles of CyaA chromatographed on the TSK column. In these conditions the inventors observed multimeric forms eluting from 9 to 13 mL and a significant fraction of a monomeric species eluting between 13 and 15 mL (M: 180±20 kDa). The hydrodynamic radius of this monomeric CyaA species measured by dynamic light scattering was 5.3±0.3 nm. The monomeric holo-CyaA toxin was also stable for long-term storage at −20° C. as its hydrodynamic radius and its retention volume by SEC were identical before and after thawing.

The impact of the initial concentration of CyaA was further analyzed on the multimer/monomer ratio. Samples of CyaA at concentrations of 12, 5, 2.5 or 1 μM in 8 M urea were loaded on the TSK column equilibrated in buffer B. FIG. 4C shows that the proportion of monomers versus multimers was dependent upon the initial concentration of the urea-unfolded CyaA loaded onto the column. The four SEC profiles of CyaA show that the fraction of multimers increased with the initial CyaA concentration, suggesting that the multimer formation is an aggregative process.

FIG. 5A compares the UV-profiles on SEC-TDA obtained by the three methods used to refold CyaA, i.e., by dialysis, by buffer exchange onto G-25 or by direct loading onto the TSK column. It is noteworthy that the proportion of monomers appears to be related to the molecular confinement during refolding as a higher fraction of monomeric CyaA was obtained with the TSK matrix with smaller particle size (8 μm) as compared to G-25 matrix (52 μm) or to the absence of confinement in the case of dialysis procedure. The TSK column is made of rigid spherical silica beads bonded with hydrophilic groups, while the Sephadex G-25 is a bead-formed gel made of epichlorohydrin cross-linked dextran. To determine whether the chemical nature of the matrix may also contribute to the formation of monomeric CyaA in addition to the confinement effect, the inventors compared results obtained on the TSK column with those obtained on a Superdex200 resin, made of cross-linked dextran and agarose with particle size of 11 μm. As shown in FIG. 5B, the urea-denatured CyaA loaded and refolded onto the Superdex200 column eluted as both multimers (8-11 mL) and monomer (12 mL) as observed with the TSK column. To further test the confinement-dependent refolding, CyaA was analyzed by SEC on Superdex200 after protein dialysis in the presence of calcium. The Superdex200 chromatogram clearly shows that dialysis of CyaA produced only multimers (FIG. 5B). These results indicate that the confinement properties of the matrix (TSK or Superdex200) rather than its chemical nature are important for efficient folding of CyaA into a monomeric form.

The confinement effect was further evaluated by comparing the CyaA folding process on Superdex200 and on a Sephacryl200 column, the latter having a similar chemical nature (agarose and dextran) and similar optimum protein separation range as the Superdex resin but with larger particle size (50±25 μm for Sephacryl vs 11 μm for Superdex). The UV profiles obtained with the Sephacryl200 and the Superdex200 (packed in the same XK16/60 column to strictly compare the experiments) are superimposed in FIG. 5C and clearly demonstrate that the confinement provided by the Superdex matrix by reducing intermolecular interactions strongly favored monomer formation as compared to the Sephacryl media, which only produced multimers. Refolding of CyaA on a Superose 6HR column made of agarose beads with particle size of 13±2 μm (similar to Superdex200) also favored the folding of the protein into a monomeric state (FIG. 5D). Taken together, these data indicate that molecular confinement during CyaA refolding on SEC may reduce intermolecular interactions between proteins and thus favor folding of the toxin into a monomeric state. The confinement properties appear rather independent of the chemical composition of the matrix (silica, agarose, dextran).

2.3. Calcium and Acylation are Required for CyaA Folding into a Monomeric Form.

Besides molecular confinement, the parameters that could affect the efficiency of formation of CyaA monomers were investigated. CyaA is known to require calcium and acylation for its toxic activities, i.e. cell lysis (hemolysis) and delivery of its catalytic domain across plasma membrane into the cell cytosol to produce cAMP (intoxication). The effect of calcium on CyaA folding is illustrated by the SEC profiles of CyaA refolded onto a Superdex200 5/150 column equilibrated in the absence or in the presence of 2 mM calcium (FIG. 6A). The comparison of the SEC profiles shows that the presence of calcium was crucial for CyaA refolding. The refolding properties of pro-CyaA, i.e., the toxin without acyl chains, were then investigated (FIG. 6B). The post-translational acylation of pro-CyaA, leading to the mature CyaA protein, is well known to be essential for toxin activity. However, its impact on the folding of CyaA has never been investigated. The molecular mass of pro-CyaA in 4 M urea was first measured. The SEC-TDA data showed that pro-CyaA was monomeric in 4 M urea (not shown), as observed for the acylated CyaA (FIG. 2A). The SEC profile of pro-CyaA upon refolding onto Superdex200 in the presence of 2 mM calcium shows two species (FIG. 6B, thick trace), the main peak corresponding to large multimers and the second peak, appearing as a shoulder on the main peak of multimers, corresponds to species of smaller sizes. However, in marked contrast to the acylated CyaA (FIG. 6A, thick trace), no distinct peak corresponding to a monomeric pro-CyaA species could be evidenced. Finally, refolding of CyaA and pro-CyaA in the absence of calcium was also examined and showed that both proteins refolded in EDTA led to the formation of multimers (FIGS. 6A and 6B, dashed traces). Collectively, these data indicate that besides molecular confinement, both acylation and calcium are required to produce high yields of CyaA monomers.

2.4. Structural and Functional Characterization of the Monomeric State of CyaA

The secondary structure content of the monomeric CyaA species isolated from the SEC-assisted folding procedure was then analyzed by synchrotron radiation circular dichroism. The far-UV CD spectrum of CyaA is typical of an alpha/beta protein (FIG. 7), as suggested by the CD spectrum deconvolution performed by K2D3. The secondary structure content estimation obtained from the deconvolution is close to the secondary structure content of CyaA predicted by SOPMA (see legend of FIG. 7). The inventors also analyzed the far-UV CD spectrum of the multimeric CyaA species. Both monomers and multimers exhibit similar far-UV CD spectra (inset FIG. 7) indicating that the secondary structure content of CyaA is not significantly affected by the oligomerisation state (quaternary structure) of the molecule.

Finally, the biological activities of the different CyaA species were compared using sheep erythrocytes as model target cells. Two fractions of CyaA eluted from the Superdex200 column (FIG. 5C), corresponding to oligomeric species (fraction O, eluting at 7-9 ml) and monomeric species (fraction M, eluting at 12-13 ml) were independently pooled, concentrated and assayed for activity. For each species, both the hemolytic activity (i.e. ability to lyze cells) and the capacity of the toxin to increase intracellular cAMP (invasive activity) were monitored as a function of protein concentrations. CyaA refolded by rapid buffer exchange on G25 in the absence and in the presence of calcium was also tested in parallel. FIG. 8 shows that the refolded monomeric CyaA (fraction M) displayed the highest hemolytic and cytotoxic activities: its specific hemolytic and cytotoxic activities were about 20-25 times higher than that of the multimeric fractions (fraction O). CyaA refolded by rapid buffer exchange on G25 in the presence of calcium (triangles) exhibited similar hemolysis activity as the oligomers from SEC and was rather inefficient to induce cAMP production (FIG. 8B, triangles). CyaA refolded by rapid buffer exchange on G25 in the absence of calcium had no hemolytic nor cytotoxic activities, in agreement with previous data showing that calcium is required for both activities.

It should be noted that the hemolytic activity shows a cooperativity (n~3) in agreement with prior reports suggesting that pore formation requires oligomerisation of the protein in the membrane. In contrast the accumulation of intracellular cAMP did not display any cooperativity, in line with the idea that the competent form able to translocate its catalytic domain across the plasma membrane is the monomeric state of CyaA. All together these data indicate that the refolded, monomeric state of CyaA exhibits the highest hemolytic and cell-invasive activities and might be therefore considered as the genuine, functionally active form of the toxin.

2.5. Stability of hCyaAm Over Time Followed by Size Exclusion Chromatography The stability of hCyaAm at 25° C. as a function of time was investigated to estimate its stability at room temperature in the presence of various concentrations of calcium in the buffer. For this purpose, hCyaAm was desalted in buffer A: 20 mM Hepes, 150 mM NaCl, pH 7.4 in the absence of calcium or containing 0.2 and 0.5 mM CaCl2. The samples (hCyaAm with 2, 0.5, 0.2 and 0 mM $CaCl_2$) were loaded into a capillary loop of an Akta pure system and injected at various time points into a Superdex 200 10/300 column equilibrated at the same calcium concentration as the protein sample. The species of proteins are named based on their retention volumes, i.e., multimers (8-9 mL), oligomers (9-11 mL) and monomers (11-13 mL). The proportions of each species as a function of time were plotted (FIG. 9). The data show that hCyaAm in the presence of calcium from 2 to 0.2 mM is stable for more than 72 hours (3 days) at 25° C. In the absence of calcium in the buffer (see data: hCyaAm wo calcium), the population of monomers decreases faster, indicating that hCyaAm stability is weaker. However, the monomers are stable for at least 24 hours in the absence of any calcium in the buffer.

The Inventors then buffer-exchanged hCyaAm on a G25 column equilibrated with 0.2 mM EDTA. In this case, the buffer of the protein sample containing 2 mM CaCl2 was replaced by 0.2 mM EDTA. The representation of the three species as a function of time clearly highlights the conversion of monomers to multimers with a half time of approximately one hour. In the presence of EDTA, any calcium released by hCyaAm is irreversibly chelated while in the sample devoid of calcium and EDTA (FIG. 9D, samples wo calcium), any calcium ion released by hCyaAm remains free in solution and available for protein binding assuming the equilibrium constant is reached. Hence, the depletion of calcium ions from hCyaAm induces the aggregation of the protein (FIG. 10).

Collectively, the data show that hCyaAm is stable as a monomer at 25° C. for more than three days in the presence of calcium ($CaCl_2$>0.2 mM), and for at least one day in the absence of calcium in the buffer and for less than one hour in the presence of EDTA.

The same experiments were done with the CyaA-OVA protein to evaluate the effect of epitope insertion in the catalytic domain of CyaA. CyaA-OVA in 6M urea was used to produce urea-free, monomeric hCyaA-OVAm. A batch of hCyaA-OVAm was desalted in buffer (20 mM Hepes, 150 mM NaCl, pH 7.4) containing various concentrations of $CaCl_2$. The proportion of species as a function of time at various calcium concentrations is shown in FIG. 11. These data clearly show that hCyaA-OVAm is less stable than hCyaAm, suggesting that the insertion of the OVA epitope in the catalytic domain slightly or locally destabilizes CyaA. However, the destabilizing effect is relatively weak if we consider that for calcium concentrations higher than 0.5 mM, more than 90% of CyaA remains monomeric after 24 hours.

2.6. Limited Proteolysis of hCyaAm Followed by Mass Spectrometry

To identify the weakly stable and solvent-exposed regions of CyaA, limited proteolysis of hCyaAm was performed, followed by mass spectrometry. Proteolysis was done at a trypsin:CyaA ratio of 1:40 in the presence of 2 or 0.5 mM CaCl2 and quenched at various time points by AEBSF and frozen into liquid nitrogen. Mass spectrometry analysis of the samples is shown in FIGS. 12 and 13.

In the presence of 2 mM calcium (FIG. 12), the most flexible and solvent-exposed regions are located in the catalytic domain (1-400), the translocation region (400-500) and in the acylation region (750-1000). Then, the RTX domain (1000-1706) is progressively proteolyzed, suggesting that this region is buried into the toxin.

In the presence of 0.5 mM CaCl2 (FIG. 13), the catalytic domain is chopped to pieces in 30 minutes, the acylation region and the RTX domain are partially proteolyzed since the first time points. The regions from the RTX domain mostly affected covered residues 1350-1500, i.e., the RTX Block IV and its flanking regions and the N-terminal parts of the RTX Blocks II and III as well as their respective flanking regions.

2.7. Temperature-Induced Unfolding of hCyaAm Followed by Tryptophan Fluorescence The stability of hCyaAm was investigated as a function of calcium concentration against thermal unfolding. An example of temperature unfolding of hCyaAm is shown in FIG. 14. At low temperature, the folded state of hCyaAm is accumulated while at high temperature, after the transition, the unfolded state is populated. The half melting temperature, Tm, is the temperature at which half of the protein is denaturated. The denaturation of hCyaAm was performed at several concentrations of calcium and the Tm values were extracted (FIG. 15).

In the presence of 150 mM NaCl, the Tm values increase with the calcium concentration from 43° C. to a plateau around 82° C. ($\Delta Tm=39°$ C.). The half transition, $Tm_{1/2}$, is reached around 60° C. at a calcium concentration, $Ca_{Tm1/2}$, of 1.23 mM. It is proposed that calcium ions decrease the entropy of the toxin and hence stabilize its folded conformation at the expense of the thermally unfolded state.

In the presence of 50 mM NaCl, the Tm values increase with the calcium concentration from 42° C. to a plateau around 90° C. ($\Delta Tm=48°$ C.). The half transition, $Tm_{1/2}$, is reached around 66° C. at a calcium concentration, $Ca_{Tm1/2}$, of 0.52 mM. These data clearly indicate that ionic strength acts as a competitor for calcium binding sites of hCyaAm: from 150 to 50 mM NaCl, the $Tm_{1/2}$ is shifted by 6° C. while the $Ca_{Tm1/2}$ is shifted by a factor of 2.

The effects of molecular confinement were also tested using the crowding agent Ficoll70 in buffer A (150 mM NaCl). The data show that the addition of 100 g/L of Ficoll70 stabilize the native state of hCyaAm at the expense of its unfolded state as observed by the shift of the Tm toward higher values.

It is proposed that the excluded volume effect due to the presence of Ficol170 disfavors the large unfolded state of CyaA, thus favoring the compact and folded state at higher temperatures than in the absence of molecular crowding agent.

2.8. Hemolysis of Erythrocytes by hCyaAm Compared to Other States of CyaA WT and CyaA-OVA.

The hemolytic activity of CyaA in different states was tested on erythrocytes (FIG. 16). In the presence of 2 mM calcium (FIG. 16A), hCyaAm, hCyaA-OVAm and CyaA in urea exhibit hemolytic dose-responses on red blood cells at protein concentrations higher than 1 μg/mL (5.6 nM). Multimers also induce hemolysis but at higher concentrations of toxins. This lower activity of the multimeric batch may result from the presence of hemolytic monomers in the (inactive) multimer batch or to an intrinsically weaker hemolytic activity of the multimers as compared to the monomers.

Monomers and multimers of CyaA and CyaA-OVA as well as CyaA in 6M urea (desalted in the presence of calcium) have been desalted on G25 (against 20 mM Hepes, 150 mM NaCl, pH 7.4) to remove free calcium from the buffer of the samples and then incubated with erythrocytes in the absence and in the presence of 2 mM EDTA. In the absence of calcium and EDTA in the RBC buffer (i.e., in 20 mM Hepes, 150 mM NaCl, pH 7.4), CyaA preserved its hemolytic activity (FIG. 16B). In the presence of EDTA, the monomeric species hCyaAm and hCyaA-OVAm are hemolytic at the tested concentrations while CyaA refolded on G25 from 6M urea solution does not exhibit hemolytic activity (FIG. 16C).

3. Conclusions

The present inventors herein show that CyaA is unfolded and monomeric in urea concentration higher than 4 M (FIG. 2), with a hydrodynamic radius of 12±2 nm, in good agreement with the expected hydrodynamic radius for a protein of 177 kDa unfolded in urea (8). The folding of CyaA in the presence of calcium, as revealed by the acquisition of secondary structure elements and the formation of solvent-exposed hydrophobic patches, occurs at urea concentrations lower than 4 M and is essentially completed at 2 M (FIG. 1). Characterization of the hydrodynamic properties of the protein refolded upon urea removal either through dialysis, dilution or rapid buffer exchange on desalting column, indicated that in all these conditions CyaA mainly formed multimers, from tetramers to higher order oligomers, as reported earlier (41,49).

Furthermore, they found that refolding of urea-unfolded CyaA by size-exclusion chromatography on resin/gels with small particle and pore sizes (beads of different chemical natures with diameters from 8 to 15 μm on average) resulted in a significant fraction of the molecules eluting as a monomeric species with an apparent hydrodynamic radius of 5.3±0.3 nm, as determined by dynamic light scattering. Interestingly, the fraction of monomeric species thus obtained appeared to be inversely correlated with the protein concentration of the sample loaded on the SEC column, suggesting that the formation of CyaA multimers is likely an aggregative process. This aggregation propensity is probably due to the appearance of solvent-exposed hydrophobic surfaces during the refolding process as indicated by the ANS studies. More importantly, the folding of CyaA into a monomeric form was found to be critically dependent upon the presence of calcium as well as on the post-translational acylation of the protein.

They further showed that, although the secondary structure content of the monomeric and multimeric species is rather similar, the monomeric form displayed about 20-25 times higher hemolytic and cytotoxic (i.e. ability to increase intracellular cAMP in target cells) activities than the multimeric ones. This suggests that the refolded CyaA monomer is the genuine, physiologically active form of the toxin. Interestingly, the hemolytic activity shows a marked cooperativity (n~3) as a function of CyaA monomer concentration, indicating that, in accordance with prior studies, the membrane permeabilizing capacity requires oligomerisation of the toxin. Yet, the fact that the monomeric protein exhibits a much higher lytic potency than the multimeric forms, suggests that the oligomerisation of the molecules may take place within the membrane, once the polypeptides have been inserted in the bilayer. This suggests that the conformation of oligomers formed once CyaA monomers partition into membranes are different from CyaA multimers formed in solution. This is at variance with the proposal of Sebo and colleagues who suggested that the lytic activity of CyaA may be carried out by a dedicated oligomeric conformation of CyaA, pre-existing in solution, while the invasive activity would be mainly displayed by a distinct monomeric conformation. The lack of cooperativity observed here for intracellular cAMP accumulation, suggests that the monomeric CyaA is indeed the competent form able to translocate its catalytic domain across the plasma membrane of the target cells.

The present data provide a rational explanation for many prior observations on CyaA structure-function relationships and may also have important implications for the understanding of the role of calcium and acylation in the biological functions of other RTX cytolysins (22). Indeed, it has been known for many years that RTX cytolysins such as CyaA, HlyA, LktA, etc . . . , are synthetized as inactive precursors that are converted to their cytotoxic forms upon acylation by dedicated acyltransferase, (CyaC, HlyC, LktC, etc . . . ) and that their cytotoxic/cytolytic activities are critically dependent upon the presence of calcium (22,23). Others previously showed that calcium is essential for folding of the CyaA RTX-domain, RD, which is important for protein interaction with the CyaA receptor and/or with target cell membrane. The present work indicates that calcium binding to the RD domain directly contributes to the overall folding of the full-length toxin into a monomeric, active species. It is likely that in the presence of calcium, RD can acquire its calcium-bound 3D structure that can then serve as a nucleation site for further folding of the upstream CyaA regions, i.e. the central hydrophobic and N-terminal catalytic domains. Incidentally, this proposed sequential refolding scheme fits nicely with the currently proposed view that CyaA, like other RTX proteins, is secreted by the type I secretion machinery (T1SS) in a vectorial C- to N-terminal manner, with its C-terminus reaching first the external, calcium-rich environment. Calcium-dependent folding of the secreted RD domain likely begins as it emerges from the secretion channel and while the remaining CyaA polypeptide is still in transit in the T1SS machinery. The folded RD may thus drive the progressive folding of the upstream CyaA regions as they exit the secretory channel. This co-secretional folding of CyaA at the mouth of the T1SS machinery could contribute to the confinement of the toxin molecules and thus prevent their potential aggregation at the bacterial surface. Interestingly, Gray et al. showed that only the toxin that is actively secreted by B. pertussis by the T1SS pathway is able to invade eukaryotic cells. It is tempting to speculate that this invasive, actively secreted species described by these authors indeed correspond to the monomeric CyaA toxin.

Besides calcium and molecular confinement, a major finding reported here is that CyaA acylation appears to be critical for toxin folding into the monomeric form. Indeed, the present inventors were not able to produce proCyaA monomers and to isolate them from multimers, as was done with the acylated CyaA. These results thus establish for the first time, a direct structural role for the acyl chains in the CyaA acquisition of a biologically functional conformation, independently of, or in addition to, their putative role(s) in membrane insertion. This result is in line with the seminal observation of Rogel et al. (41) who first reported the purification of the toxic form of adenylate cylase from B. pertussis extracts. By gel filtration, they resolved the enzymatic activity into two peaks, one major peak of high molecular weight (>700 kDa) and a minor peak, with an apparent size of 200 kDa. They showed that, although both fractions contained the same CyaA polypeptide, only the small-size fraction could induce cAMP accumulation in target cells (41). As the CyaA polypeptide expressed in Escherichia coli also lack the ability to induce cAMP accumulation in target cells, they postulated that a post-translational modification should occur in *B. pertussis* but not in *E. coli*, to confer cytotoxic capabilities to CyaA. The CyaC modifying acyltransferase and the specific acylation of CyaA on lysine residues 860 and 983 were soon described by E. Hewlett and colleagues (19). Yet, how this modification could convert the non-cytotoxic pro-CyaA into an invasive and hemolytic protein has remained elusive until now (22, 23). Similar observations have been reported for other RTX cytolysins, in particular for HlyA, but the putative contribution of the acyl chains in the cytolytic activites of these toxins is also unknown. It is generally assumed that the acyl chains could insert into the lipid bilayer to favor toxin partitioning to the plasma membrane of target cells (59). Alternatively, the acyl groups might play a structural role in maintaining the toxins in a partially folded conformation competent for membrane insertion (22,23). Yet no strong experimental evidences for this hypothesis have been obtained thus far. Herlax and Bakas tentatively proposed that the acylation may maintain HlyA in a molten globule conformation favorable for membrane insertion, but their experimental data barely support such a conclusion.

The present work shows that the acyl chains and calcium binding accelerate the kinetics of CyaA refolding and thus favor the overall formation of functional monomeric species at the expense of the less-active multimeric ones. The presence of hydrophobic acyl chains on CyaA may significantly modify the local free-energy landscape of the polypeptide chain. Shielding of these acyl chains into a nascent hydrophobic core may have a major thermodynamic contribution in restricting the temporal and conformational spaces accessible to CyaA upon refolding. Similarly, it provides direct evidence that calcium binding is mandatory for the formation of monomers, probably by kinetically favoring native folding and burying of hydrophobic regions, while in the absence of calcium, a slower kinetics of folding into the apo-state may favor intermolecular interactions between folding intermediates and would thus increase the population of multimer species.

BIBLIOGRAPHIC REFERENCES

1. Ladant, D., Brezin, C., Alonso, J. M., Crenon, I., and Guiso, N. (1986) *Bordetella pertussis* adenylate cyclase. Purification, characterization, and radioimmunoassay. *J Biol Chem* 261, 16264-16269
2. Karimova, G., Fayolle, C., Gmira, S., Ullmann, A., Leclerc, C., and Ladant, D. (1998) Charge-dependent translocation of *Bordetella pertussis* adenylate cyclase toxin into eukaryotic cells: implication for the in vivo delivery of CD8(+) T cell epitopes into antigen-presenting cells. *Proc Natl Acad Sci USA* 95, 12532-12537
3. 
4. Chenal, A., Karst, J. C., Sotomayor Perez, A. C., Wozniak, A. K., Baron, B., England, P., and Ladant, D. (2010) Calcium-induced folding and stabilization of the intrinsically disordered RTX domain of the CyaA *toxin. Biophys J* 99, 3744-3753
5. Sotomayor Perez, A. C., Karst, J. C., Davi, M., Guijarro, J. I., Ladant, D., and Chenal, A. (2010) Characterization of the regions involved in the calcium-induced folding of the intrinsically disordered RTX motifs from the *Bordetella pertussis* adenylate cyclase toxin. *Journal of molecular biology* 397, 534-549
6. Karst, J. C., Sotomayor Perez, A. C., Guijarro, J. I., Raynal, B., Chenal, A., and Ladant, D. (2010) Calmodulin-induced conformational and hydrodynamic changes in the catalytic domain of *Bordetella pertussis* adenylate cyclase toxin. *Biochemistry* 49, 318-328
7. Chenal, A., Guijarro, J. I., Raynal, B., Delepierre, M., and Ladant, D. (2009) RTX calcium binding motifs are intrinsically disordered in the absence of calcium: implication for protein secretion. *J Biol Chem* 284, 1781-1789
8. Sotomayor-Perez, A. C., Ladant, D., and Chenal, A. (2011) Calcium-induced folding of intrinsically disordered repeat-in-toxin (RTX) motifs via changes of protein charges and oligomerization states. *J Biol Chem* 286, 16997-17004
9. Karst, J. C., Sotomayor-Perez, A. C., Ladant, D., and Chenal, A. (2012) Estimation of intrinsically disordered protein shape and time-averaged apparent hydration in native conditions by a combination of hydrodynamic methods. *Methods in molecular biology* 896, 163-177
10. Sotomayor-Perez, A. C., Karst, J. C., Ladant, D., and Chenal, A. (2012) Mean net charge of intrinsically disordered proteins: experimental determination of protein valence by electrophoretic mobility measurements. *Methods in molecular biology* 896, 331-349
11. Karst, J. C., Barker, R., Devi, U., Swann, M. J., Davi, M., Roser, S. J., Ladant, D., and Chenal, A. (2012) Identification of a region that assists membrane insertion and translocation of the catalytic domain of *Bordetella pertussis* CyaA toxin. *J Biol Chem* 287, 9200-9212
12. Ladant, D., and Ullmann, A. (1999) *Bordatella pertussis* adenylate cyclase: a toxin with multiple talents. *Trends in microbiology* 7, 172-176
13. Vojtova, J., Kamanova, J., and Sebo, P. (2006) Bordetella adenylate cyclase toxin: a swift saboteur of host defense. *Curr Opin Microbiol* 9, 69-75
16. Sakamoto, H., Bellalou, J., Sebo, P., and Ladant, D. (1992) *Bordetella pertussis* adenylate cyclase toxin. Structural and functional independence of the catalytic and hemolytic activities. *J Biol Chem* 267, 13598-13602
17. Subrini, O., Sotomayor-Perez, A. C., Hessel, A., Spiaczka-Karst, J., Selwa, E., Sapay, N., Veneziano, R., Pansieri, J., Chopineau, J., Ladant, D., and Chenal, A. (2013) Characterization of a membrane-active peptide from the *Bordetella pertussis* CyaA
19. Barry, E. M., Weiss, A. A., Ehrmann, I. E., Gray, M. C., Hewlett, E. L., and Goodwin, M. S. (1991) *Bordetella pertussis* adenylate cyclase toxin and hemolytic activities require a second gene, cyaC, for activation. *J Bacteriol* 173, 720-726
22. Welch, R. A. (2001) RTX toxin structure and function: a story of numerous anomalies and few analogies in toxin biology. *Current topics in microbiology and immunology* 257, 85-111
23. Linhartova, I., Bumba, L., Masin, J., Basler, M., Osicka, R., Kamanova, J., Prochazkova, K., Adkins, I., Hejnova-Holubova, J., Sadilkova, L., Morova, J., and Sebo, P. (2010) RTX proteins: a highly diverse family secreted by a common mechanism. *FEMS Microbiol Rev* 34, 1076-1112
24. Rose, T., Sebo, P., Bellalou, J., and Ladant, D. (1995) Interaction of calcium with *Bordetella pertussis* adenylate cyclase toxin. Characterization of multiple calcium-binding sites and calcium-induced conformational changes. *J Biol Chem* 270, 26370-26376
26. Sotomayor-Perez, A. C., Subrini, O., Hessel, A., Ladant, D., and Chenal, A. (2013) Molecular Crowding Stabilizes Both the Intrinsically Disordered Calcium-Free State and the Folded Calcium-Bound State of a Repeat in Toxin (RTX) Protein. *Journal of the American Chemical Society* 135, 11929-11934

27. Baumann, U., Wu, S., Flaherty, K. M., and McKay, D. B. (1993) Three-dimensional structure of the alkaline protease of *Pseudomonas aeruginosa*: a two-domain protein with a calcium binding parallel beta roll motif. *EMBO J*12, 3357-3364

28. Meier, R., Drepper, T., Svensson, V., Jaeger, K. E., and Baumann, U. (2007) A calcium-gated lid and a large beta-roll sandwich are revealed by the crystal structure of extracellular lipase from *Serratia marcescens*. *J Biol Chem* 282, 31477-31483
29. Satchell, K. J. (2011) Structure and function of MARTX toxins and other large repetitive RTX proteins. Annual review of microbiology 65, 71-90
30. Masure, H. R., Au, D. C., Gross, M. K., Donovan, M. G., and Storm, D. R. (1990) Secretion of the *Bordetella pertussis* adenylate cyclase from *Escherichia coli* containing the hemolysin operon. Biochemistry 29, 140-145
31. Guermonprez, P., Khelef, N., Blouin, E., Rieu, P., Ricciardi-Castagnoli, P., Guiso, N., Ladant, D., and Leclerc, C. (2001) The adenylate cyclase toxin of *Bordetella pertussis* binds to target cells via the alpha(M)beta(2) integrin (CD11b/CD18). *J Exp Med* 193, 1035-1044
32. Rogel, A., and Hanski, E. (1992) Distinct steps in the penetration of adenylate cyclase toxin of *Bordetella pertussis* into sheep erythrocytes. Translocation of the toxin across the membrane. *J Biol Chem* 267, 22599-22605
35. Paccani, S. R., Finetti, F., Davi, M., Patrussi, L., D'Elios, M. M., Ladant, D., and Baldari, C. T. (2011) The *Bordetella pertussis* adenylate cyclase toxin binds to T cells via LFA-1 and induces its disengagement from the immune synapse. *J Exp Med* 208, 1317-1330
36. Guermonprez, P., Ladant, D., Karimova, G., Ullmann, A., and Leclerc, C. (1999) Direct delivery of the *Bordetella pertussis* adenylate cyclase toxin to the MHC class I antigen presentation pathway. *J Immunol* 162, 1910-1916
40. Gordon, V. M., Young, W. W., Jr., Lechler, S. M., Gray, M. C., Leppla, S. H., and Hewlett, E. L. (1989) Adenylate cyclase toxins from *Bacillus anthracis* and *Bordetella pertussis*. Different processes for interaction with and entry into target cells. *J Biol Chem* 264, 14792-14796
41. Rogel, A., Schultz, J. E., Brownlie, R. M., Coote, J. G., Parton, R., and Hanski, E. (1989) *Bordetella pertussis* adenylate cyclase: purification and characterization of the toxic form of the enzyme. *Embo J* 8, 2755-2760
42. Veneziano, R., Rossi, C., Chenal, A., Devoisselle, J. M., Ladant, D., and Chopineau, J. (2013) *Bordetella pertussis* adenylate cyclase toxin translocation across a tethered lipid bilayer. *Proc Natl Acad Sci USA* 110, 20473-20478
43. Uribe, K. B., Etxebarria, A., Martin, C., and Ostolaza, H. (2013) Calpain-Mediated Processing of Adenylate Cyclase Toxin Generates a Cytosolic Soluble Catalytically Active N-Terminal Domain. *PLoS One* 8, e67648
44. Heveker, N., and Ladant, D. (1997) Characterization of mutant *Bordetella pertussis* adenylate cyclase toxins with reduced affinity for calmodulin. Implications for the mechanism of toxin entry into target cells. *European journal of biochemistry/FEBS* 243, 643-649
45. Benz, R., Maier, E., Ladant, D., Ullmann, A., and Sebo, P. (1994) Adenylate cyclase toxin (CyaA) of *Bordetella pertussis*. Evidence for the formation of small ion-permeable channels and comparison with HlyA of *Escherichia coli*. *J Biol Chem* 269, 27231-27239
47. Hewlett, E. L., Donato, G. M., and Gray, M. C. (2006) Macrophage cytotoxicity produced by adenylate cyclase toxin from *Bordetella pertussis*: more than just making cyclic AMP! *Molecular microbiology* 59, 447-459
49. Gentile, F., Knipling, L. G., Sackett, D. L., and Wolff, J. (1990) Invasive adenylyl cyclase of *Bordetella pertussis*. Physical, catalytic, and toxic properties. *J Biol Chem* 265, 10686-10692
52. Hewlett, E. L., Urban, M. A., Manclark, C. R., and Wolff, J. (1976) Extracytoplasmic adenylate cyclase of *Bordetella pertussis*. *Proc Natl Acad Sci USA* 73, 1926-1930

53. Sebo, P., Glaser, P., Sakamoto, H., and Ullmann, A. (1991) High-level synthesis of active adenylate cyclase toxin of *Bordetella pertussis* in a reconstructed *Escherichia coli* system. *Gene* 104, 19-24

54. Dadaglio, G., Morel, S., Bauche, C., Moukrim, Z., Lemonnier, F. A., Van Den Eynde, B. J., Ladant, D., and Leclerc, C. (2003) Recombinant adenylate cyclase toxin of *Bordetella pertussis* induces cytotoxic T lymphocyte responses against HLA*0201-restricted melanoma epitopes. *Int Immunol* 15, 1423-1430
55. Preville, X., Ladant, D., Timmerman, B., and Leclerc, C. (2005) Eradication of established tumors by vaccination with recombinant *Bordetella pertussis* adenylate cyclase carrying the human papillomavirus 16 E7 oncoprotein. *Cancer Res* 65, 641-649
56. Saron, M. F., Fayolle, C., Sebo, P., Ladant, D., Ullmann, A., and Leclerc, C. (1997) Anti-viral protection conferred by recombinant adenylate cyclase toxins from *Bordetella pertussis* carrying a CD8+ T cell epitope from lymphocytic choriomeningitis virus. *Proc Natl Acad Sci USA* 94, 3314-3319
59. Welch, R. A. (1991) Pore-forming cytolysins of gram-negative bacteria. *Molecular microbiology* 5, 521-528
60. El-Azami-El-Idrissi M. et al., *J. Biol. Chem.* 2003; October 3; 278(40):38514-21.
61. Needleman and Wunsch. *J.Mol. Biol.* 48,443-453, 1970
62. Guiso et al (*Microbial pathogenesis* 1989, 7(5):373-80
63. Linhartová I, et al. (2010) *FEMS Microbiol Rev.*, 34:1076-1112

The invention claimed is:

1. A method to produce a solution of monomeric, stable and functional CyaA toxin, comprising:
   A) providing a sample comprising denatured and acylated CyaA toxin, between 4M and 10M of a chaotropic agent, and between 1 and 10 mM of a calcium salt,
   B) applying said sample on a size-exclusion chromatography column having a matrix that provides molecular confinement on the CyaA toxin, in the presence of calcium, and
   C) eluting the CyaA toxin from the size-exclusion chromatography column with an elution buffer comprising a calcium salt but no chaotropic agent;
   to thereby provide a solution of monomeric, stable and functional CyaA toxin that does not contain chaotropic agent.

2. The method of claim 1, wherein said molecular confinement is achieved by size-exclusion chromatography on a matrix containing porous beads whose diameter is smaller than or equal to 10 μm.

3. The method of claim 1, wherein said monomeric CyaA toxin consists of non-aggregated monomers having a molecular mass of about 177 kDa.

4. The method of claim 1, wherein said solution comprises more than 75% of said monomeric, stable and functional CyaA toxin.

5. The method of claim 1, wherein said eluted stable CyaA toxin remains non-aggregated upon long-term storage up to 6 months.

6. The method of claim 1, wherein the molecular confinement is achieved by size-exclusion chromatography on a matrix containing porous beads whose diameter is smaller than or equal to 10 μm, said beads containing pores whose diameter is smaller than 0.1 μm.

7. The method of claim 1, wherein the CyaA toxin is a detoxified toxin that retains the ability to translocate its catalytic domain into target cells.

8. The method of claim 1, wherein said elution occurs in a buffer of low ionic strength.

9. The method of claim 1, wherein said elution occurs in a buffer having a neutral to basic pH.

10. A solution obtained by the method of claim 1, comprising monomeric, stable and functional CyaA toxin and not comprising a chaotropic agent; wherein more than 75% of the CyaA toxin in the solution is monomeric and has a molecular mass of about 177 kDa; and wherein the CyaA toxin is not coupled to any exogenous antigen.

11. The solution of claim 10, wherein said CyaA toxin is calcium-loaded.

12. A pharmaceutical composition comprising a) the monomeric, stable and functional CyaA toxin obtained by the method of claim 7, wherein said CyaA toxin is not coupled to any exogenous antigen; and b) a pharmaceutically acceptable carrier; wherein said pharmaceutical composition does not comprise any chaotropic agent.

13. A method of therapeutically vaccinating a subject, comprising administering the pharmaceutical composition of claim 12 to a subject in need thereof.

14. A method of delivering an antigen to a subject, comprising administering the pharmaceutical composition of claim 12 to a subject in need thereof.

15. A method of delivering a protective antigen against whooping cough to a subject, comprising administering the pharmaceutical composition of claim 12 to a subject in need thereof.

16. The method of claim 1, wherein said sample in step A) contains between 0.01-10 mg/mL of denatured and acylated CyaA.

* * * * *

SEQUENCE LISTING

```
<160> NUMBER OF SEQ ID NOS: 1

<210> SEQ ID NO 1
<211> LENGTH: 1706
<212> TYPE: PRT
<213> ORGANISM: Bordetella pertussis
<220> FEATURE:
<221> NAME/KEY: SITE
<222> LOCATION: (1)..(1706)
<223> OTHER INFORMATION: amino acid sequence of CyaA

<400> SEQUENCE: 1
```

```
Met Gln Gln Ser His Gln Ala Gly Tyr Ala Asn Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Asp Phe Glu Ala Val Lys Val
                165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                245                 250                 255

Ala Arg Arg Gln Phe Arg Tyr Asp Gly Asp Met Asn Ile Gly Val Ile
            260                 265                 270

Thr Asp Phe Glu Leu Glu Val Arg Asn Ala Leu Asn Arg Arg Ala His
        275                 280                 285

Ala Val Gly Ala Gln Asp Val Val Gln His Gly Thr Glu Gln Asn Asn
    290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
                325                 330                 335

Gln Arg Gly Glu Gly Tyr Val Phe Tyr Glu Asn Arg Ala Tyr Gly Val
            340                 345                 350

Ala Gly Lys Ser Leu Phe Asp Asp Gly Leu Gly Ala Ala Pro Gly Val
        355                 360                 365

Pro Ser Gly Arg Ser Lys Phe Ser Pro Asp Val Leu Glu Thr Val Pro
    370                 375                 380

Ala Ser Pro Gly Leu Arg Arg Pro Ser Leu Gly Ala Val Glu Arg Gln
385                 390                 395                 400

Asp Ser Gly Tyr Asp Ser Leu Asp Gly Val Gly Ser Arg Ser Phe Ser
                405                 410                 415

Leu Gly Glu Val Ser Asp Met Ala Ala Val Glu Ala Ala Glu Leu Glu
```

```
                420             425             430
Met Thr Arg Gln Val Leu His Ala Gly Ala Arg Gln Asp Asp Ala Glu
        435             440             445

Pro Gly Val Ser Gly Ala Ser Ala His Trp Gly Gln Arg Ala Leu Gln
    450             455             460

Gly Ala Gln Ala Val Ala Ala Gln Arg Leu Val His Ala Ile Ala
465             470             475             480

Leu Met Thr Gln Phe Gly Arg Ala Gly Ser Thr Asn Thr Pro Gln Glu
                485             490             495

Ala Ala Ser Leu Ser Ala Ala Val Phe Gly Leu Gly Glu Ala Ser Ser
            500             505             510

Ala Val Ala Glu Thr Val Ser Gly Phe Phe Arg Gly Ser Ser Arg Trp
        515             520             525

Ala Gly Gly Phe Gly Val Ala Gly Ala Met Ala Leu Gly Gly Gly
    530             535             540

Ile Ala Ala Ala Val Gly Ala Gly Met Ser Leu Thr Asp Asp Ala Pro
545             550             555             560

Ala Gly Gln Lys Ala Ala Gly Ala Glu Ile Ala Leu Gln Leu Thr
                565             570             575

Gly Gly Thr Val Glu Leu Ala Ser Ser Ile Ala Leu Ala Leu Ala Ala
            580             585             590

Ala Arg Gly Val Thr Ser Gly Leu Gln Val Ala Gly Ala Ser Ala Gly
        595             600             605

Ala Ala Ala Gly Ala Leu Ala Ala Ala Leu Ser Pro Met Glu Ile Tyr
    610             615             620

Gly Leu Val Gln Gln Ser His Tyr Ala Asp Gln Leu Asp Lys Leu Ala
625             630             635             640

Gln Glu Ser Ser Ala Tyr Gly Tyr Glu Gly Asp Ala Leu Leu Ala Gln
                645             650             655

Leu Tyr Arg Asp Lys Thr Ala Ala Glu Gly Ala Val Ala Gly Val Ser
            660             665             670

Ala Val Leu Ser Thr Val Gly Ala Ala Val Ser Ile Ala Ala Ala Ala
        675             680             685

Ser Val Val Gly Ala Pro Val Ala Val Thr Ser Leu Leu Thr Gly
    690             695             700

Ala Leu Asn Gly Ile Leu Arg Gly Val Gln Gln Pro Ile Ile Glu Lys
705             710             715             720

Leu Ala Asn Asp Tyr Ala Arg Lys Ile Asp Glu Leu Gly Gly Pro Gln
                725             730             735

Ala Tyr Phe Glu Lys Asn Leu Gln Ala Arg His Glu Gln Leu Ala Asn
            740             745             750

Ser Asp Gly Leu Arg Lys Met Leu Ala Asp Leu Gln Ala Gly Trp Asn
        755             760             765

Ala Ser Ser Val Ile Gly Val Gln Thr Thr Glu Ile Ser Lys Ser Ala
    770             775             780

Leu Glu Leu Ala Ala Ile Thr Gly Asn Ala Asp Asn Leu Lys Ser Val
785             790             795             800

Asp Val Phe Val Asp Arg Phe Val Gln Gly Glu Arg Val Ala Gly Gln
                805             810             815

Pro Val Val Leu Asp Val Ala Ala Gly Gly Ile Asp Ile Ala Ser Arg
            820             825             830

Lys Gly Glu Arg Pro Ala Leu Thr Phe Ile Thr Pro Leu Ala Ala Pro
        835             840             845
```

```
Gly Glu Glu Gln Arg Arg Thr Lys Thr Gly Lys Ser Glu Phe Thr
850                 855                 860

Thr Phe Val Glu Ile Val Gly Lys Gln Asp Arg Trp Arg Ile Arg Asp
865                 870                 875                 880

Gly Ala Ala Asp Thr Thr Ile Asp Leu Ala Lys Val Val Ser Gln Leu
                    885                 890                 895

Val Asp Ala Asn Gly Val Leu Lys His Ser Ile Lys Leu Asp Val Ile
                900                 905                 910

Gly Gly Asp Gly Asp Val Val Leu Ala Asn Ala Ser Arg Ile His
        915                 920                 925

Tyr Asp Gly Gly Ala Gly Thr Asn Thr Val Ser Tyr Ala Ala Leu Gly
930                 935                 940

Arg Gln Asp Ser Ile Thr Val Ser Ala Asp Gly Glu Arg Phe Asn Val
945                 950                 955                 960

Arg Lys Gln Leu Asn Asn Ala Asn Val Tyr Arg Glu Gly Val Ala Thr
                965                 970                 975

Gln Thr Thr Ala Tyr Gly Lys Arg Thr Glu Asn Val Gln Tyr Arg His
                980                 985                 990

Val Glu Leu Ala Arg Val Gly Gln Leu Val Glu Val Asp Thr Leu Glu
            995                 1000                1005

His Val Gln His Ile Ile Gly Gly Ala Gly Asn Asp Ser Ile Thr
        1010                1015                1020

Gly Asn Ala His Asp Asn Phe Leu Ala Gly Gly Ser Gly Asp Asp
        1025                1030                1035

Arg Leu Asp Gly Gly Ala Gly Asn Asp Thr Leu Val Gly Gly Glu
        1040                1045                1050

Gly Gln Asn Thr Val Ile Gly Gly Ala Gly Asp Asp Val Phe Leu
        1055                1060                1065

Gln Asp Leu Gly Val Trp Ser Asn Gln Leu Asp Gly Gly Ala Gly
        1070                1075                1080

Val Asp Thr Val Lys Tyr Asn Val His Gln Pro Ser Glu Glu Arg
        1085                1090                1095

Leu Glu Arg Met Gly Asp Thr Gly Ile His Ala Asp Leu Gln Lys
        1100                1105                1110

Gly Thr Val Glu Lys Trp Pro Ala Leu Asn Leu Phe Ser Val Asp
        1115                1120                1125

His Val Lys Asn Ile Glu Asn Leu His Gly Ser Arg Leu Asn Asp
        1130                1135                1140

Arg Ile Ala Gly Asp Asp Gln Asp Asn Glu Leu Trp Gly His Asp
        1145                1150                1155

Gly Asn Asp Thr Ile Arg Gly Arg Gly Gly Asp Asp Ile Leu Arg
        1160                1165                1170

Gly Gly Leu Gly Leu Asp Thr Leu Tyr Gly Glu Asp Gly Asn Asp
        1175                1180                1185

Ile Phe Leu Gln Asp Asp Glu Thr Val Ser Asp Asp Ile Asp Gly
        1190                1195                1200

Gly Ala Gly Leu Asp Thr Val Asp Tyr Ser Ala Met Ile His Pro
        1205                1210                1215

Gly Arg Ile Val Ala Pro His Glu Tyr Gly Phe Gly Ile Glu Ala
        1220                1225                1230

Asp Leu Ser Arg Glu Trp Val Arg Lys Ala Ser Ala Leu Gly Val
        1235                1240                1245
```

```
Asp Tyr Tyr Asp Asn Val Arg Asn Val Glu Asn Val Ile Gly Thr
    1250                1255                1260

Ser Met Lys Asp Val Leu Ile Gly Asp Ala Gln Ala Asn Thr Leu
    1265                1270                1275

Met Gly Gln Gly Gly Asp Thr Val Arg Gly Gly Asp Gly Asp
    1280                1285                1290

Asp Leu Leu Phe Gly Gly Asp Gly Asn Asp Met Leu Tyr Gly Asp
    1295                1300                1305

Ala Gly Asn Asp Thr Leu Tyr Gly Gly Leu Gly Asp Asp Thr Leu
    1310                1315                1320

Glu Gly Gly Ala Gly Asn Asp Trp Phe Gly Gln Thr Gln Ala Arg
    1325                1330                1335

Glu His Asp Val Leu Arg Gly Gly Asp Gly Val Asp Thr Val Asp
    1340                1345                1350

Tyr Ser Gln Thr Gly Ala His Ala Gly Ile Ala Ala Gly Arg Ile
    1355                1360                1365

Gly Leu Gly Ile Leu Ala Asp Leu Gly Ala Gly Arg Val Asp Lys
    1370                1375                1380

Leu Gly Glu Ala Gly Ser Ser Ala Tyr Asp Thr Val Ser Gly Ile
    1385                1390                1395

Glu Asn Val Val Gly Thr Glu Leu Ala Asp Arg Ile Thr Gly Asp
    1400                1405                1410

Ala Gln Ala Asn Val Leu Arg Gly Ala Gly Gly Ala Asp Val Leu
    1415                1420                1425

Ala Gly Gly Glu Gly Asp Asp Val Leu Leu Gly Gly Asp Gly Asp
    1430                1435                1440

Asp Gln Leu Ser Gly Asp Ala Gly Arg Asp Arg Leu Tyr Gly Glu
    1445                1450                1455

Ala Gly Asp Asp Trp Phe Phe Gln Asp Ala Ala Asn Ala Gly Asn
    1460                1465                1470

Leu Leu Asp Gly Gly Asp Gly Arg Asp Thr Val Asp Phe Ser Gly
    1475                1480                1485

Pro Gly Arg Gly Leu Asp Ala Gly Ala Lys Gly Val Phe Leu Ser
    1490                1495                1500

Leu Gly Lys Gly Phe Ala Ser Leu Met Asp Glu Pro Glu Thr Ser
    1505                1510                1515

Asn Val Leu Arg Asn Ile Glu Asn Ala Val Gly Ser Ala Arg Asp
    1520                1525                1530

Asp Val Leu Ile Gly Asp Ala Gly Ala Asn Val Leu Asn Gly Leu
    1535                1540                1545

Ala Gly Asn Asp Val Leu Ser Gly Gly Ala Gly Asp Asp Val Leu
    1550                1555                1560

Leu Gly Asp Glu Gly Ser Asp Leu Leu Ser Gly Asp Ala Gly Asn
    1565                1570                1575

Asp Asp Leu Phe Gly Gly Gln Gly Asp Asp Thr Tyr Leu Phe Gly
    1580                1585                1590

Val Gly Tyr Gly His Asp Thr Ile Tyr Glu Ser Gly Gly Gly His
    1595                1600                1605

Asp Thr Ile Arg Ile Asn Ala Gly Ala Asp Gln Leu Trp Phe Ala
    1610                1615                1620

Arg Gln Gly Asn Asp Leu Glu Ile Arg Ile Leu Gly Thr Asp Asp
    1625                1630                1635

Ala Leu Thr Val His Asp Trp Tyr Arg Asp Ala Asp His Arg Val
```

|      |      |      |      |      |      |      |      |      |      |      |      |      |      |      |
|------|------|------|------|------|------|------|------|------|------|------|------|------|------|------|
| 1640 |      |      |      |      | 1645 |      |      |      |      | 1650 |      |      |      |      |
| Glu  | Ile  | Ile  | His  | Ala  | Ala  | Asn  | Gln  | Ala  | Val  | Asp  | Gln  | Ala  | Gly  | Ile  |
| 1655 |      |      |      |      | 1660 |      |      |      |      | 1665 |      |      |      |      |
| Glu  | Lys  | Leu  | Val  | Glu  | Ala  | Met  | Ala  | Gln  | Tyr  | Pro  | Asp  | Pro  | Gly  | Ala  |
| 1670 |      |      |      |      | 1675 |      |      |      |      | 1680 |      |      |      |      |
| Ala  | Ala  | Ala  | Ala  | Pro  | Pro  | Ala  | Ala  | Arg  | Val  | Pro  | Asp  | Thr  | Leu  | Met  |
| 1685 |      |      |      |      | 1690 |      |      |      |      | 1695 |      |      |      |      |
| Gln  | Ser  | Leu  | Ala  | Val  | Asn  | Trp  | Arg  |      |      |      |      |      |      |      |
| 1700 |      |      |      |      | 1705 |      |      |      |      |      |      |      |      |      |